United States Patent [19]
Windass et al.

[11] Patent Number: 6,156,536
[45] Date of Patent: Dec. 5, 2000

[54] TOXINS FROM THE WASP *BRACON HEBETOR*

[75] Inventors: John David Windass, Finchampstead, United Kingdom; Peter Daniel Christian, Macgregor, Australia; Rachael Elizabeth Duncan, Reading, United Kingdom; Valerie Jayne Baule, Kambah, Australia

[73] Assignee: Commonwealth Scientific and Industrial Research Organisation, Campbell, Australia

[21] Appl. No.: 08/836,374

[22] PCT Filed: Nov. 21, 1995

[86] PCT No.: PCT/GB95/02720

§ 371 Date: May 12, 1997

§ 102(e) Date: May 12, 1997

[87] PCT Pub. No.: WO96/16171

PCT Pub. Date: May 30, 1996

[30] Foreign Application Priority Data

Nov. 22, 1994 [GB] United Kingdom .................. 9423540
Jan. 19, 1995 [GB] United Kingdom .................. 9501074
Jun. 29, 1995 [GB] United Kingdom .................. 9513293

[51] Int. Cl.[7] ...................................................... C12N 5/00
[52] U.S. Cl. ........................ 435/69.1; 435/325; 435/252.3
[58] Field of Search ........................ 536/23.1; 435/69.1, 435/325, 252.3, 255.1, 320.1; 530/350; 514/2

[56] References Cited

U.S. PATENT DOCUMENTS 5,874,298  2/1999  Johnson et al. ..................... 435/325

FOREIGN PATENT DOCUMENTS

WO93/03144  2/1993  WIPO .
WO93/18145  9/1993  WIPO .

OTHER PUBLICATIONS

"Purification and Characterization of Insecticidal Toxins from Venom Glads of the Parasitic Wasp, *Bracon Hebetor*," Gary Quistad et al., Insect Biochem. Molec. Biol., vol. 24, No. 10, pp. 955–961, 1994.

Chemical Abstract vol. 108, 1988, p. 248, 108: 50986v "Effect of the Toxin from the Venom of the Braconid Habrobracon Hebetor (Say), on Insect Neuromuscular Transmission," T. I. Slavnova et al.

"Characterization of Two Paralysing Protein Toxins (A–MTX and B–MTX), Isolated from a Homogenate of the Wasp Microbracon Hebetor (Say)," B. J. Visser et al., Comp. Biochem. Physio. V75B, No. 3, pp. 523–530, 1983.

*Primary Examiner*—Karen Cochrane Carlson
*Attorney, Agent, or Firm*—McDermott, Will & Emery

[57] ABSTRACT

Novel insect toxins obtainable from *Bracon hebetor*, including DNA sequences which encode therefor, a recombinant DNA construct which comprises at least one DNA sequence which encodes said toxins, and a biological control agent comprising said recombinant DNA construct.

18 Claims, 19 Drawing Sheets

Fig.3.

Absorbance (280 nm) vs Elution volume (mls)

Markers: 670,000; 158,000; 44,000; 17,000; 1,350

Fig.4.

Log(x) of standard vs $K_{av}$

- Thyroglobulin
- γ-globulin
- BrhTX-1
- Ovalbumin
- Myoglobin
- Vitamin B-12

Fig.6.

Subunit BrhTX-1

| Residue | (a) | (b) | (c) | (d) |
|---|---|---|---|---|
| 1 | Phe | Thr | Met | Ile |
| 2 | Asn | Leu | Asp | Ile |
| 3 | Pro | Phe | Asp | Asn |
| 4 | Glu | Thr | Gly | Gly |
| 5 | Thr | Asp | Glu | His |
| 6 | His | Arg | - | Asp |
| 7 | Arg | Lys | - | Ala |
| 8 | Glu | Trp* | Glu | Thr |
| 9 | - | Ser* | - | Glu |
| 10 | Lys | Gly | - | Glu |
| 11 | Asn | Arg | Met | Gln |
| 12 | Tyr | Ala | Asn | Phe |
| 13 | - | Asp | Pro* | Pro |
| 14 | Ala | Lys* | - | Pro* |
| 15 | Lys | Thr* | - | Thr* |
| 16 | Glu | Phe | Asp* | Ala |
| 17 | His | Gly | - | Tyr |
| 18 | Gly | Pro | - | Met* |
| 19 | Glu | - | - | Thr* |
| 20 | Glu | - | - | Arg* |
| 21 | | | | Met* |
| 22 | | | | Ala |
| 23 | | | | Arg* |
| 24 | | | | Asn |
| 25 | | | | Val |

Fig.7.

|  | PHE | ASN | PRO | GLU | THR | HIS | ARG | GLU | — | LYS | ASN | TYR | — | ALA | LYS | GLU | HIS | GLY | GLU | GLU |
|---|---|---|---|---|---|---|---|---|---|---|---|---|---|---|---|---|---|---|---|---|
| BH(a)A | TTC<br>T | AAC<br>T | CCI | GAA<br>G | ACI | CAC<br>T | IGI | GA | | | | | | | | | | | | |
| BH(a)B | | | | | | | | | | | | | | | | | | | | |
| BH(a)I | TTC | AAC | CCI | GAA<br>G | ACI | CAC | IGI | GAA<br>G | III | AAA<br>G | AAC | TAC | III | GCI | AAA<br>G | GAA<br>G | CAT<br>G | GGI | GAA<br>G | GA<br>G |

(BH(a)B row: GCI AAA GAA CAC GGI GAA GA, with variants G, G, T, G, G)

Fig.8.

```
          10        20        30        40        50        60
           |         |         |         |         |         |
    CCAGTGAATTCGCNNCCGCTTTGGATAAATCATGAAATTTTTATATCTAATACTCCTTTT
         EcoRI  NotI
                                             M  K  F  L  Y  L  I  L  L 70        80        90       100       110       120
           |         |         |         |         |         |
    AATTGCAGGAGTAGTATCATTCAATCCGGAGACACATCGTGAATGTAAGAATTATTGCGC

I  A  G  V  V  S  F  N  P  E  T  H  R  E  C  K  N  Y  C  A 130       140       150       160       170       180
           |         |         |         |         |         |
    CAAAGAGCACGGCGAGGAATATCGTACGTGGTCTTTCCGTTACGAACTTGGTGATATTTT

K  E  H  G  E  E  Y  R  T  W  S  F  R  Y  E  L  G  D  I  F 190       200       210       220       230       240
           |         |         |         |         |         |
    TAAATGTGTTTGCACTCACGGAAAGAATCTTATGGGAAGCGAGAATTATGGTAAGTGTAG

K  C  V  C  T  H  G  K  N  L  M  G  S  E  N  Y  G  K  C  R 250       260       270       280       290       300
           |         |         |         |         |         |
    AGAAGCATGTATTCAAAATCATGGAGCGGGAGGCTTTAAATATGCCTTTCCCATATACAG

E  A  C  I  Q  N  H  G  A  G  G  F  K  Y  A  F  P  I  Y  S 310       320       330       340       350       360
           |         |         |         |         |         |
    CGAAGTACCAGCATCATGGGCATGCATATCACTCAGGAGAAAAATAAGACATTTTGTATA

```
      370       380       390       400       410       420
       |         |         |         |         |         |
CATGCTTGCTCAGAAATTCATCACAAGGCCCCACCTAAGAATCCCATAGTTATGAAAAAT

M   L   A   Q   K   F   I   T   R   P   H   L   R   I   P   -

430       440       450       460       470       480
       |         |         |         |         |         |
GGACAATGCTACTACCAAGATCACAGGGGTGTTGACAGGTATTGTGAAGTTTATATGAAG 490       500       510       520       530       540
       |         |         |         |         |         |
TTCTTAGATGCGTTGGAATCAATTTAACAATGATCAAATTCATGTTATCAATGAAGGAAG 550       560       570       580       590       600
       |         |         |         |         |         |
AATAATGAATTAATAATAATTATCAAAAATCAAAAAAAAAAAGCGGCCGCGAATTCGAGC
                                            NotI    EcoRI 610       620       630       640       650       660
       |         |         |         |         |         |
TCGGTACCCGGGGATCCTCTAGAGTCGACCTGCAGGTCATGCAACTTGGCGTAATCATGG 670       680
       |         |
TCATAGCTGTTTCCTGTGTGAAA
```

Fig.9.

```
        ILE  ILE  ASN  GLY  HIS  ASP  ALA  THR  GLU  GLU  GLN  PHE  PRO  PRO  THR  ALA  TYR  MET  THR

BH(d)A  ATI  ATI  AAC  GGI  CAC  GAC  GCI  AC
                       T       T    T

BH(d)B                           GAC  GCI  ACI  GAA  GAA  CAA  TTC  CC
                                           T          G    G    G    T

BH(d)I  ATI  ATI  AAC  GGI  CAT  GAC  GCI  ACI  GAA  GAA  CAA  TTC  CCI  CCI  ACI  GCI  TAC  ATG  ACI
                       T            T                 G    G    G                             T

ARG  MET  ALA  ARG  ASN  VAL

BH(d)I  IGI  ATG  GCI  IGI  AAC  GT
                                 T
```

Fig.10.

```
                  27                                                                54
GGT TTT TCC CAG TCA CGA CGT TGT AAA ACG ACG GCC AGT GAA TTC GCG GCC GCT
CCA AAA AGG GTC AGT GCT GCA ACA TTT TGC TGC CGG TCA CTT AAG CGC CGG CGA
                                                            EcoRI 81                                       108
GTT GAT ATA TAA CAA TTT ATT AAA AAT TTC AAG TGG AAA GAA AAA CTA TCT TGT
CAA CTA TAT ATT GTT AAA TAA TTT TTA AAG TTC ACC TTT CTT TTT GAT AGA ACA 135                                               162
TTT TTT TTT TGT TTT TTT TCA TAA TTT AAA ATG CAT TTC TTC GCC TCC ATC CTG
AAA AAA AAA ACA AAA AAA AGT ATT AAA TTT TAC GTA AAG AAG CGG AGG TAG GAC
                                          M   H   F   F   A   S   I   L 189                                      216
GTA TCC TTC TTA CTG GGC AAG GCA ATT CAT GAT GTG GAA GGA ATA ATA AAT GGT
CAT AGG AAG AAT GAC CCG TTC CGT TAA GTA CTA CAC CTT CCT TAT TAT TTA CCA
 V   S   F   L   L   G   K   A   I   H   D   V   E   G   I   I   N   G 243                                      270
CAT GAT GCT ACT GAG GGA CAA TTT CCC CAT ATG GCT TAT TTA CAA GCA TCA GCT
GTA CTA CGA TGA CTC CCT GTT AAA GGG GTA TAC CGA ATA AAT GTT CGT AGT CGA
 H   D   A   T   E   G   Q   F   P   H   M   A   Y   L   Q   A   S   A
```

Fig.10 (Cont-1).

```
                              297                                                                     324
GGA AAG TGT TCT TAT GTA TGT GGC GGT GCT CTT CTA ACT AAA AAA CAT ATT ATG
CCT TTC ACA AGA ATA CAT ACA CCG CCA CGA GAA GAT TGA TTT TTT GTA TAA TAC
 G   K   C   S   Y   V   C   G   G   A   L   L   T   K   K   H   I   M 351                                                                     378
ACA GCT GCT CAT TGT GTA GCA ATG CAC AGA ACG GGA AAT ATT AAA GTA GCC CTT
TGT CGA CGA GTA ACA CAT CGT TAC GTG TCT TGC CCT TTA TAA TTT CAT CGG GAA
 T   A   A   H   C   V   A   M   H   R   T   G   N   I   K   V   A   L 405                                                                     432
GGT GTT ACG GAT TTT CAT AAT AAG CCA TCA ATG CAA CAA AGA AAG GTT GAA CAT
CCA CAA TGC CTA AAA GTA TTA TTC GGT AGT TAC GTT GTT TCT TTC CAA CTT GTA
 G   V   T   D   F   H   N   K   P   S   M   Q   Q   R   K   V   E   H 459                                                                     486
ATA AAA GTC CAT TCT GAG TAC AAA GGA GGA AGG CGT AAG TCA TTA AAA AAT TGG
TAT TTT CAG GTA AGA CTC ATG TTT CCT CCT TCC GCA TTC AGT AAT TTT TTA ACC
 I   K   V   H   S   E   Y   K   G   G   R   R   K   S   L   K   N   W 513                                                                     540
TAT CGC TCC ATA CAT CGT ACA TTT ACA GGA CCG TCT GGG GAT AAA GAA TAC AAT
ATA GCG AGG TAT GTA GCA TGT AAA TGT CCT GGC AGA CCC CTA TTT CTT ATG TTA
 Y   R   S   I   H   R   T   F   T   G   P   S   G   D   K   E   Y   N 567                                                                     594
GAT ATT GCT ATT ATA ACG TTG AGC CAG GAA GTA ACA CTA GGA CCA GTA GTA AAG
CTA TAA CGA TAA TAT TGC AAC TCG GTC CTT CAT TGT GAT CCT GGT CAT CAT TTC
 D   I   A   I   I   T   L   S   Q   E   V   T   L   G   P   V   V   K
```

Fig.10 (Cont-2).

```
             621                                                          648
ACT ATT AAT TTA CCC CCA AAG AGC TAT CGG CTT CCT TTT GAT CAA GAT GCT AGA
TGA TAA TTA AAT GGG GGT TTC TCG ATA GCC GAA GGA AAA CTA GTT CTA CGA TCT
 T   I   N   L   P   P   K   S   Y   R   L   P   F   D   Q   D   A   R 675                                                          702
TTG TCG GGC TTT GGG CGA ACA GTC ATT GTC AAA GAA AAT GAT CCA ATT CCT CCA
AAC AGC CCG AAA CCC GCT TGT CAG TAA CAG TTT CTT TTA CTA GGT TAA GGA GGT
 L   S   G   F   G   R   T   V   I   V   K   E   N   D   P   I   P   P 729                                                          756
CCC ACT ACA CAT TTA CAA TGG CTA GAT ATG AAG GTT CTT CAT TCA CGA GAT GCT
GGG TGA TGT GTA AAT GTT ACC GAT CTA TAC TTC CAA GAA GTA AGT GCT CTA CGA
 P   T   T   H   L   Q   W   L   D   M   K   V   L   H   S   R   D   A 783                                                          810
ATT GTC ACT GAT AGT GAA TTT CTC GCT GAT AAA GAA TAT GGT GAT GGA ACT TGG
TAA CAG TGA CTA TCA CTT AAA GAG CGA CTA TTT CTT ATA CCA CTA CCT TGA ACC
 I   V   T   D   S   E   F   L   A   D   K   E   Y   G   D   G   T   W 837                                                          864
TCT AAT GCA GCT AAG GGA GAC AGC GGT AGT CCC TTA GTC AAG GAT AAT CAA GTA
AGA TTA CGT CGA TTC CCT CTG TCG CCA TCA GGG AAT CAG TTC CTA TTA GTT CAT
 S   N   A   A   K   G   D   S   G   S   P   L   V   K   D   N   Q   V
```

Fig.10 (Cont-3).

```
            891                                                    918
ATT GGC GTA GCC GTT TCT GTG AGT GAT GAA GAA CAT ACT ACA CGC TTT CAA ATA
TAA CCG CAT CGG CAA AGA CAC TCA CTA CTT CTT GTA TGA TGT GCG AAA GTT TAT
 I   G   V   A   V   S   V   S   D   E   E   H   T   T   R   F   Q   I 945                                                    972
GTC ACT TAT TAT TTG GAT TGG ATC AAG AAA TAT GCC GAA CTT GCG TAA AAA GAA
CAG TGA ATA ATA AAC CTA ACC TAG TTC TTT ATA CGG CTT GAA CGC ATT TTT CTT
 V   T   Y   Y   L   D   W   I   K   K   Y   A   E   L   A 999                                                   1026
TAA AGA GCA AAA TTG CTC AGA TGG TGA ATA TAC ATT TTT CCA ATA AGC TCA GAA
ATT TCT CGT TTT AAC GAG TCT ACC ACT TAT ATG TAA AAA GGT TAT TCG AGT CTT 1053                                                   1080
AAA ATC GAT TTA TAT GTA ATT AAA AAA ATT AAA GAT TGT TTT TTC TCT TTT AAC
TTT TAG CTA AAT ATA CAT TAA TTT TTT TAA TTT CTA ACA AAA AAG AGA AAA TTG

1107
AGA AGA ATT TGG CGN NCG TGA ATT CGA GCT CGG TAC CCG GGG
TCT TCT TAA ACC GCN NGC ACT TAA GCT CGA GCC ATG GGC CCC
                         EcoRI
```

Fig.11.

```
AATTTTTCCTCATAACAATGTCAATCATATGTAAAATAATCTTGTTGGTGCTACTGAGTT
---------+---------+---------+---------+---------+---------+   60
TTAAAAAGGAGTATTGTTACAGTTAGTATACATTTTATTAGAACAACCACGATGACTCAA
 F  F  L  I  T  M  S  I  I  C  K  I  I  L  L  V  L  L  S  W

BH(b)C
                     >>>>
GGACATCGATGGTATCGTCAACATTATTTACAGACCGAAAGTGGTGTGGACGTGCCGATA
---------+---------+---------+---------+---------+---------+   120
CCTGTAGCTACCATAGCAGTTGTAATAAATGTCTGGCTTTCACCACACCTGCACGGCTAT
  T  S  M  V  S  S  T  L  F  T  D  R  K  W  C  G  R  A  D  K

AGACTTTTGGTCCTTCACGGTCGCTAGGAGGAGGTGTTGGTGATTGCTGCAGAAGTCATG
---------+---------+---------+---------+---------+---------+   180
TCTGAAAACCAGGAAGTGCCAGCGATCCTCCTCCACAACCACTAACGACGTCTTCAGTAC
  T  F  G  P  S  R  S  L  G  G  G  V  G  D  C  C  R  S  H  D  -

ACAGCTGTGGCCGCATGATTAAACCAGGAGAGACTTATGGAGATGTTACGAATAAAGGAT
---------+---------+---------+---------+---------+---------+   240
TGTCGACACCGGCGTACTAATTTGGTCCTCTCTGAATACCTCTACAATGCTTATTTCCTA
                            BH(b)D<<<<
  S  C  G  R  M  I  K  P  G  E  T  Y  G  D  V  T  N  K  G  F

TTTCAAATATGTAATGTCTGATGATTATTACCAACACTAAATCTTGATTAAGAAGCTGTA
---------+---------+---------+---------+---------+---------+   300
AAAGTTTATACATTACAGACTACTAATAATGGTTGTGATTTAGAACTAATTCTTCGACAT
  S  N  M  *  C  L  M  I  I  T  N  T  K  S  *  L  R  S  C  K

AAAATATCATTTTGAGGAAATACTCGATATTTTTACTTTCCTCCGAATGTTATTTCTTCA
---------+---------+---------+---------+---------+---------+   360
TTTTATAGTAAAACTCCTTTATGAGCTATAAAAATGAAAGGAGGCTTACAATAAAGAAGT
  N  I  I  L  R  K  Y  S  I  F  L  L  S  E  C  Y  F  F  S

GCTTTTCAACTAAAATTTCTTAATCAACTTGACAATTGTTAAAAATAACATATTTAATTA
---------+---------+---------+---------+---------+---------+   420
CGAAAAGTTGATTTTAAAGAATTAGTTGAACTGTTAACAATTTTTATTGTATAAATTAAT
  F  S  T  K  I  S  *  S  T  *  Q  L  L  K  I  T  Y  L  I  M

TGATTATTATTTATTTGATTAAAGTTGGGAAAAAAAAAACTG
---------+---------+---------+---------+---   462
ACTAATAATAAATAAACTAATTTCAACCCTTTTTTTTTGAC
  I  I  I  Y  L  I  K  V  G  K  K  K  T
```

Fig.12.

```
CACGCCTACTTAGATAATTTCTCAATTCTTTGCAAATTATGAAATAAGTGCAAGAGATGT
----------+---------+---------+---------+---------+---------+   60
GTGCGGATGAATCTATTAAAGAGTTAAGAAACGTTTAATACTTTATTCACGTTCTCTACA
  R  L  L  R  *  F  L  N  S  L  Q  I  M  K  *  V  Q  E  M  C  -

GTATGACACCTCAATCTGAGTTTGTTCATAATTCGAGAGGGATAAATAAGGAAGTCTCTG
----------+---------+---------+---------+---------+---------+  120
CATACTGTGGAGTTAGACTCAAACAAGTATTAAGCTCTCCCTATTTATTCCTTCAGAGAC
  M  T  P  Q  S  E  F  V  H  N  S  R  G  I  N  K  E  V  S  V  -

TGTACAAAAGAAAACTACCTCATATAAATCTTGCATTTTTCCGTGAGAGAGAAAAAAAAA
----------+---------+---------+---------+---------+---------+  180
ACATGTTTTCTTTTGATGGAGTATATTTAGAACGTAAAAAGGCACTCTCTCTTTTTTTTT
  Y  K  R  K  L  P  H  I  N  L  A  F  F  R  E  R  E  K  K  T  -

CCCTGAAAAACTGAGTAAGGCAATAATTTTXCCTCATAACAATGTCAATCATATGTAAAA
----------+---------+---------+---------+---------+---------+  240
GGGACTTTTTGACTCATTCCGTTATTAAAAXGGAGTATTGTTACAGTTAGTATACATTTT
  L  K  N  *  V  R  Q  *  F  ?  L  I  T  M  S  I  I  C  K  I  -

TAATCTTGTTGGTGCTACTGAGTTGGACATCGATGGTATCGTCAACATTATTTACAGACC
----------+---------+---------+---------+---------+---------+  300
ATTAGAACAACCACGATGACTCAACCTGTAGCTACCATAGCAGTTGTAATAAATGTCTGG
  I  L  L  V  L  L  S  W  T  S  M  V  S  S  T  L  F  T  D  R  -

GAAAGTGGTGTGGACGTGCCGATAAGACTTTTGGTCCTTCACGGTCGCTAGGAGGAGGTG
----------+---------+---------+---------+---------+---------+  360
CTTTCACCACACCTGCACGGCTATTCTGAAAACCAGGAAGTGCCAGCGATCCTCCTCCAC
  K  W  C  G  R  A  D  K  T  F  G  P  S  R  S  L  G  G  G  V  -

TTGGTGATTGCTGCAGAAGTCATGACAGCTGTGGCCGCATGATTAAACCAGGAGAGACTT
----------+---------+---------+---------+---------+---------+  420
AACCACTAACGACGTCTTCAGTACTGTCGACACCGGCGTACTAATTTGGTCCTCTCTGAA
  G  D  C  C  R  S  H  D  S  C  G  R  M  I  K  P  G  E  T  Y  -
```

Fig.12 (Cont-1).

```
ATGGAGATGTTACGAATAAAGGATTTTCAAATATTTGGGAATGCCGATGTGACTATGCAT
----------+---------+---------+---------+---------+---------+   480
TACCTCTACAATGCTTATTTCCTAAAAGTTTATAAACCCTTACGGCTACACTGATACGTA
 G  D  V  T  N  K  G  F  S  N  I  W  E  C  R  C  D  Y  A  F  -

TTTTTCAATGTCTTCAGCGTTCCAATGGTAAAATGAAAAATGTTGTGGAAATATTGCATT
----------+---------+---------+---------+---------+---------+   540
AAAAAGTTACAGAAGTCGCAAGGTTACCATTTTACTTTTTACAACACCTTTATAACGTAA
 F  Q  C  L  Q  R  S  N  G  K  M  K  N  V  V  E  I  L  M  F  -

TTGACGTTGTCAATACACCCTGTTACTTCATGAAAGATGGCCGTGCTAAAATATCACCCC
----------+---------+---------+---------+---------+---------+   600
AACTGCAACAGTTATGTGGGACAATGAAGTACTTTCTACCGGCACGATTTTATAGTGGGG
 D  V  V  N  T  P  C  Y  F  M  K  D  G  R  A  K  I  S  P  H  -

ATACTGTATATGATAAACACGAATCACTCTATCAACTTATACTACACAAAGATAATTTTA
----------+---------+---------+---------+---------+---------+   660
TATGACATATACTATTTGTGCTTAGTGAGATAGTTGAATATGATGTGTTTCTATTAAAAT
 T  V  Y  D  K  H  E  S  L  Y  Q  L  I  L  H  K  D  N  F  K  -

AGGAGTGGGTGCATGATAATGCTCTTCTCCCGCAAGAGCTGGGGATTAAAGATGAGCATG
----------+---------+---------+---------+---------+---------+   720
TCCTCACCCACGTACTATTACGAGAAGAGGGCGTTCTCGACCCCTAATTTCTACTCGTAC
 E  W  V  H  D  N  A  L  L  P  Q  E  L  G  I  K  D  E  H  V  -

TGTGGGAGACACTGATGGCATGGATGGACTTTAGATTTCCAACTGAATAATAAATATTCC
----------+---------+---------+---------+---------+---------+   780
ACACCCTCTGTGACTACCGTACCTACCTGAAATCTAAAGGTTGACTTATTATTTATAAGG
 W  E  T  L  M  A  W  M  D  F  R  F  P  T  E  *  *  I  F  Q  -

AAATACAGATATCCTTTTGATAAAATGTCGTAAACATGATTGTTTAGATGAATGGTAAAT
----------+---------+---------+---------+---------+---------+   840
TTTATGTCTATAGGAAAACTATTTTACAGCATTTGTACTAACAAATCTACTTACCATTTA
 I  Q  I  S  F  *  *  N  V  V  N  M  I  V  *  M  N  G  K  L  -

TAATGAAAAGATTGATTGAAAATGTCTGAAGTAACTXXXGGATXXGACATATAATATATA
----------+---------+---------+---------+---------+---------+   900
ATTACTTTTCTAACTAACTTTTACAGACTTCATTGAXXXCCTAXXCTGTATATTATATAT
 M  K  R  L  I  E  N  V  *  S  N  ?  ?  ?  ?  H  I  I  Y  N  -
```

Fig.12 (Cont-2).

```
ATATTTGCCTTATTXGATAAACTTCTACCXTTAAXAAAGGAAAAAGGAGGAGGXGTAGGA
----------+---------+---------+---------+---------+---------+   960
TATAAACGGAATAAXCTATTTGAAGATGGXAATTXTTTCCTTTTTCCTCCTCCXCATCCT
   I  C  L  I  ?  *  T  S  T  ?  ?  K  G  K  R  R  R  ?  R  R

GGAGGATTAGGATATTTTACAAGGATTTTAAAAATAATTAAACAATTAGATCTTCTGTAA
----------+---------+---------+---------+---------+---------+  1020
CCTCCTAATCCTATAAAATGTTCCTAAAATTTTTATTAATTTGTTAATCTAGAAGACATT
   R  I  R  I  F  Y  K  D  F  K  N  N  *  T  I  R  S  S  V  N

ATTGATTGATCATGTATTAAATACAATAACATCTCGTTCTCATAGTACAATGAAAAAGAA
----------+---------+---------+---------+---------+---------+  1080
TAACTAACTAGTACATAATTTATGTTATTGTAGAGCAAGAGTATCATGTTACTTTTTCTT
   *  L  I  M  Y  *  I  Q  *  H  L  V  L  I  V  Q  *  K  R  T  -

CATAACAGTATGCACAAAAATAATGACGGTAAATATCTATGTATGTATGTAGAGAGAAGA
----------+---------+---------+---------+---------+---------+  1140
GTATTGTCATACGTGTTTTTATTACTGCCATTTATAGATACATACATACATCTCTCTTCT
   *  Q  Y  A  Q  K  *  *  R  *  I  S  M  Y  V  C  R  E  K  K  -

AAATAAAAATAGTTAGACAGGTACCAAAAAAAAAAAAAAAAAAAAAAAAAAAAAAAAAAA
----------+---------+---------+---------+---------+--------   1197
TTTATTTTTATCAATCTGTCCATGGTTTTTTTTTTTTTTTTTTTTTTTTTTTTTTTTTTT
   I  K  I  V  R  Q  V  P  K  K  K  K  K  K  K  K  K         -
```

Fig.13.

```
  1   MSIICKIILL VLLSWTSMVS STLFTDRKWC GRADKTFGPS RSLGGGVGDC

51   CRSHDSCGRM IKPGETYGDV TNKGFSNIWE CRCDYAFFQC LQRSNGKMKN

101   VVEILHFDVV NTPCYFMKDG RAKISPHTVY DKHESLYQLI LHKDNFKEWV

151   HDNALLPQEL GIKDEHVWET LMAWMDFRFP TE*
```

Fig. 14.

```
   1  CACGCCTACT TAGATAATTT CTCAATTCTT TGCAAATTAT GAAATAAGTG
  51  CAAGAGATGT GTATGACACC TCAATCTGAG TTTGTTCATA ATTCGAGAGG
 101  GATAAATAAG GAAGTCTCTG TGTACAAAAG AAAACTACCT CATATAAATC
 151  TTGCATTTTT CCGTGAGAGA GAAAAAAAAA CCCTGAAAAA CTGAGTAAGG
 201  CAATAATTTT CCCTCATAAC AATGTCAATC ATATGTAAAA TAATCTTGTT
 251  GGTGCTACTG AGTTGGACAT CGATGGTATC GTCAACATTA TTTACAGACC
 301  GAAAGTGGTG TGGACGTGCC GATAAGACTT TTGGTCCTTC ACGGTCGCTA
 351  GGAGGAGGTG TTGGTGATTG CTGCAGAAGT CATGACAGCT GTGGCCGCAT
 401  GATTAAACCA GGAGAGACTT ATGGAGATGT TACGAATAAA GGATTTTCAA
 451  ATATTTGGGA ATGCCGATGT GACTATGCAT TTTTTCAATG TCTTCAGCGT
 501  TCCAATGGTA AAATGAAAAA TGTTGTGGAA ATATTGCATT TTGACGTTGT
 551  CAATACACCC TGTTACTTCA TGAAAGATGG CCGTGCTAAA ATATCACCCC
 601  ATACTGTATA TGATAAACAC GAATCACTCT ATCAACTTAT ACTACACAAA
 651  GATAATTTTA AGGAGTGGGT GCATGATAAT GCTGGAACTC TTCTCCCGCA
 701  AGAGCTGGGG ATTAAAGATG AGCATGTGTG GGAGACACTG ATGGCATGGA
 751  TGGACTTTAG ATTTCCAACT GAATAATAAA TATTCCAAAT ACAGATATCC
 801  TTTTGATAAA ATGTCGTAAA CATGATTGTT TAGATGAATG GTAAATTAAT
 851  GAAAGATTG ATTGAAAATG TCTGAAGTAA CTTTTGGATT TTACATATAA
 901  TATATAATAT TTGCCTTATT TGATAAACTT CTAAATTAAA AAAGAAAAAG
 951  GAGGAGGAGT AGGAGGAGGA TTAGGATATT TTACAAGGAT TTTAAAAATA
1001  ATTAAACAAT TAGATCTTCT GTAAATTGAT TGATCATGTA TTAAATACAA
1051  TAACATCTCG TTCTCATAGT ACAATGAAAA AGAACATAAC AGTATGCACA
1101  AAAATAATGA CGGTAAATAT CTATGTATGT ATGTAGAGAG AAGAAAATAA
1151  AAATAGTTAG ACAGGTACCA AAAAAAAAAA AAAAAAAAAA AAAAAAAAA
1201  A
```

```
   1  MSIICKIILL VLLSWTSMVS STLFTDRKWC GRADKTFGPS RSLGGGVGDC
  51  CRSHDSCGRM IKPGETYGDV TNKGFSNIWE CRCDYAFFQC LQRSNGKMKN
 101  VVEILHFDVV NTPCYFMKDG RAKISPHTVY DKHESLYQLI LHKDNFKEWV
 151  HDNAGTLLPQ ELGIKDEHVW ETLMAWMDFR FPTE*
```

Fig. 15.

```
?       (T)
G  I   A   Q   D   V   G   H   A   A   H   S   F   T   K
  ATT GCT CAA GAT GTT GGT CAT GCT GCT CAT TCT TTC ACT AAA
      C   C   G   C   C   A   C   C   C   C   AGC T   C   G
      A   A       A   A   A       A   A       G       T   A
      G   A       G   G   G       G   G       A       C   G
      G                   G           G           G (H)
(G)  V   H   N   P   G   N   F   R
    GTT CAT AAT CCA GGT AAT TTC AGA
        C   C   C   C   A   C   T
        A               G   C       T   C
        G               T   G       G
```

Fig. 16.

GTGCACAATCCAGGAAACTTCCGAGTCTCCAAATGTGTATGCGACATTGCGCTCAAGGAGTGCC

TCACTACTCATCCTGAAATGAGTTTCAAATTTGTTAAAGCACTCTTTTTTGATTTGCTTGCTCC

ACCCTGTTTTGATCAGATTGCTGATTGGGGTAAGAAAAAATTGAAAAATAAGCAGGCATTTTCA

CTGCATGATTTACAATCAGCTGCCCACGCGCTCTGGCAAACACTCTATGACGCTGTCAAGGGCA

TAGCTCAAGATGTCGGCCA

Fig. 17 (Cont).

```
AATCAGCTGCCCACGCGCTCTGGCAAACACTCTATGACGCTGTCAAGGGCATAGCTCAGG
---------+---------+---------+---------+---------+---------+
TTAGTCGACGGGTGCGCGAGACCGTTTGTGAGATACTGCGACAGTTCCCGTATCGAGTCC
  S   A   A   H   A   L   W   Q   T   L   Y   D   A   V   K   G   I   A   Q   D   -

ATGTCGGACATGCTGCACATTCTTTTGAAAAAATGTTACAGTAACAGTTAAATATGAAAA
---------+---------+---------+---------+---------+---------+
TACAGCCTGTACGACGTGTAAGAAAACTTTTTTACAATGTCATTGTCAATTTATACTTTT
  V   G   H   A   A   H   S   F   E   K   M   L   Q

AGGTCCATGATAGTAGAATACAGTTATTGTTGTATAAATAAATAATATATTCAGAATGAT
---------+---------+---------+---------+---------+---------+
TCCAGGTACTATCATCTTATGTCAATAACAACATATTTATTTATTATATAAGTCTTACTA

AAAAAAAAA
---------  669
TTTTTTTTT
```

Fig.17

```
AAAAGACTAAAAATAAGAAAAAAAAACATAGAAGAATGTTTACAATAATTTATATTTTA
----------+---------+---------+---------+---------+---------+
TTTTCTGATTTTTATTCTTTTTTTTGTATCTTCTTACAAATGTTATTAAATATAAAAAT
  K  T  K  N  K  K  K  H  R  R  M  F  T  I  I  Y  I  F  K

AACTTTCATTTCTATTAGTTCCGTGCTGGAGTTTTTCAACCTACGCTGGGTATGGTGAAT
----------+---------+---------+---------+---------+---------+
TTGAAAGTAAAGATAATCAAGGCACGACCTCAAAAAGTTGGATGCGACCCATACCACTTA
  L  S  F  L  L  V  P  C  W  S  F  S  T  Y  A  G  Y  G  E  Y

ATAATCGGTCCATTACTAAGCGACAGATGGACGATGGTGAGACGTGCGAAAGGTGTTTGA
----------+---------+---------+---------+---------+---------+
TATTAGCCAGGTAATGATTCGCTGTCTACCTGCTACCACTCTGCACGCTTTCCACAAACT
  N  R  S  I  T  K  R  Q  M  D  D  G  E  T  C  E  R  C  L  N -

ATCCACTCGAATTAGTAAATGACGCTGTAGACTCGTGCATTGAAGCTCATGAGGAATGTG
----------+---------+---------+---------+---------+---------+
TAGGTGAGCTTAATCATTTACTGCGACATCTGAGCACGTAACTTCGAGTACTCCTTACAC
  P  L  E  L  V  N  D  A  V  D  S  C  I  E  A  H  E  E  C  E -

AGGAATTCATTGAAGGCGGGATGGAAATGCTTCATGTACACAATCCAGGAAACTTCCGAG
----------+---------+---------+---------+---------+---------+
TCCTTAAGTAACTTCCGCCCTACCTTTACGAAGTACATGTGTTAGGTCCTTTGAAGGCTC
  E  F  I  E  G  G  M  E  M  L  H  V  H  N  P  G  N  F  R  V -

TCTCCAAATGTGTATGCGACATTGCGCTCAAGGAGTGCCTCACTACTCATCCTGAAATGA
----------+---------+---------+---------+---------+---------+
AGAGGTTTACACATACGCTGTAACGCGAGTTCCTCACGGAGTGATGAGTAGGACTTTACT
  S  K  C  V  C  K  I  A  L  K  E  C  L  T  T  H  P  E  M  S -

GTTTCAAATTTGTTAAAGCACTCTTTTTTGATTTGCTTGCTCCACCCTGTTTTGATCAGA
----------+---------+---------+---------+---------+---------+
CAAAGTTTAAACAATTTCGTGAGAAAAAACTAAACGAACGAGGTGGGACAAAACTAGTCT
  F  K  F  V  K  A  L  F  F  D  L  L  A  P  P  C  F  D  Q  I -

TTGCTGATTGGGGTAAGAAAAAATTGAAAAATAAGCAGGCATTTTCACTGCATGATTTAC
----------+---------+---------+---------+---------+---------+
AACGACTAACCCCATTCTTTTTTAACTTTTTATTCGTCCGTAAAAGTGACGTACTAAATG
  A  D  W  G  K  K  K  L  K  N  K  Q  A  F  S  L  H  D  L  Q -
```

TOXINS FROM THE WASP *BRACON HEBETOR*

The present invention relates to novel insect toxins, DNA sequences encoding proteins which are toxic to insects, recombinant DNA constructs which comprise DNA sequences which encode a protein which is toxic to insects, and a biological control agent comprising said insect toxins, DNA sequences or recombinant DNA constructs.

The venoms of many social wasps have been extensively studied and are known to contain a potent array of biologically active amines, pain-producing neuropeptides, allergens and neurotoxins (Piek (1991) *Toxicon*, 29, 139–149). Much less understood are the venoms of solitary wasps, especially those which lead a parasitic lifestyle. Many solitary parasitic wasps prey upon insects and more than 250 species have been observed to paralyse their host (for review see Piek and Spanjer (1986) *Venoms of the Hymenoptera*, T Piek (Ed.) Academic Press, London pp161–307). Many of these species are in the family Braconidae. The majority of braconid wasps are primary parasites. Adults lay their eggs almost exclusively in or on other insects and, after hatching, the wasp larvae feed upon their host. One braconid species that has attracted attention is *Bracon hebetor* (Bracon=Microbracon=Habrobracon). *Bracon hebetor* (*B. hebetor*) is a small (3 mm) parasite of Lepidoptera larvae which have a cryptic, or cocooning, lifestyle. Adult female wasps deposit eggs on the outside of host larvae while simultaneously injecting a paralysing venom. Within minutes, the host larvae become uncoordinated and eventually suffer complete paralysis. Although not directly fatal, this paralysis is permanent and immobilises the insect until the wasp larvae emerge to feed upon their host. The venom of *B. hebetor* possesses an extremely potent paralysing activity. In larvae of the greater waxmoth, *Galleria mellonella* (*G. mellonella*), it has been estimated that complete and permanent paralysis occurs at levels of 1 part venom to 200,000,000 parts host haemolypmph (Beard (1952) *Conn. Agric. Exp. Stn. New Haven Bulletin*, 562, 27). Furthermore, the venom shows selective toxicity towards insects and between insect orders. Spider, crayfish, frog, rat and guinea-pig neuromuscular preparations all appear to be insensitive to the venom (Rathmayer and Walther (1976) *Animal, Plant and Microbial Toxins,* 2, Plenum Press, New York, 299–307; Deitmer (1973) *Die Wirkung des Griffes der Schlupf-wespe Habrobracon Say auf die neuromuskulare Ubertragung am sartoriusmuskel des Frosches*, Diplomarbeit, Universitat Bonn).

The paralysing component of *B. hebetor* venom is thought to act by presynaptically blocking excitatory glutamatergic transmission at neuromuscular junctions, possibly by inhibiting the release of synaptic vesicles (Walther and Reinecke (1983) *Neuroscience,* 9, 213–224; Piek and Mantel (1970) *Comp. Gen. Pharmcol,* 1, 87–92; Piek (1966) *J. Insect Physiol.,* 12, 561–568).

Venoms from many arthropods that prey on insects have been found to contain toxins which selectively act on insects. Such insect-selective neurotoxins can be important molecular tools to study insect neurobiology. The mode of action and insect-selectivity of *B. hebetor* toxin predicts that it could be useful in the study of neuromuscular transmission in Lepidoptera and in the study of vesicle release at Lepidopteran neuromuscular junctions. It will also be appreciated that such insect selectivity is very advantageous in the control of insect pests. However, since the published information on proteinaceous toxins from *B. hebetor* suggests that multiple toxins may exist it was first necessary to purify and characterise a toxin that had high neurotoxic activity to Lepidopteran larvae. We have now purified and characterised two neurotoxic proteins, which for ease of reference only have been designated bracon toxin 1 and 2 (hereinafter BrhTX-1, and BrhTX-2).

Thus, according to one aspect of the present invention there is provided an insect toxin comprising four polypeptide subunits, wherein the polypeptide subunits have the N terminal amino acid sequences shown in Sequence ID Nos. 1, 2, 3 and 4.

This insect toxin corresponds to BrhTX-1.

According to another aspect of the present invention there is provided an insect toxin obtainable from a parasitic wasp having estimated molecular weights of about 34,000 Da, about 21,000 Da, about 18,500 Da and about 17,000 Da as measured by an SDS-polyacrylamide gel electrophoresis method as defined herein.

This insect toxin corresponds to the toxin designated BrhTX-2.

We have also isolated and characterised the polypeptide subunits of at least BrhTX-1.

Thus according to another aspect of the present invention there is provided isolated DNA comprising the nucleic acid sequence as shown in Sequence ID No. 19; sequences which show 60% or more homology with the nucleic acid sequence as shown in Sequence ID No. 19; sequences which hybridise to the nucleic acid sequence as shown in Sequence ID No. 19; and sequences which are degenerate as a result of the genetic code to the nucleic acid as shown in Sequence ID No. 19 and encode the same polypeptide.

According to yet another aspect of the present invention there is provided isolated DNA comprising the nucleic acid sequence as shown in Sequence ID No. 46; sequences which show 60% or more homology with the nucleic acid sequence as shown in Sequence ID No. 46; sequences which hybridise to the nucleic acid sequence as shown in Sequence ID No 46; and sequences which are degenerate as a result of genetic code to the nucleic acid as shown in Sequence ID No. 46 and encode the same polypeptide.

According to a further aspect of the present invention there is provided isolated DNA comprising the nucleic acid sequence as shown in Sequence ID No. 57; sequences which show 60% or more homology with the nucleic acid sequence as shown in Sequence ID No. 57; sequences which hybridise to the nucleic acid sequence as shown in Sequence ID No. 57; and sequences which are degenerate as a result of the genetic code to the nucleic acid as shown in Sequence ID No. 57 and encode the same polypeptide.

According to a yet further aspect of the present invention there is provided isolated DNA comprising the nucleic acid sequence as shown in Sequence ID No. 36; sequences which show 60% or more homology with the nucleic acid sequence as shown in Sequence ID No. 36; sequences which hybridise to the nucleic acid sequence as shown in Sequence ID No. 36; and sequences which are degenerate as a result of the genetic code to the nucleic acid as shown in Sequence ID No. 36 and encode the same polypeptide.

The DNA of the present invention may be cDNA, genomic DNA or synthesised DNA.

As mentioned above, the present invention includes DNA which shows 60% or more homology to the DNA sequences of the present invention. Preferably ≧65%, more preferably ≧70%, even more preferably ≧75% or ≧80% of the nucleotides are common. Especially preferred are sequences showing 85%, 90%, 95%, or 99% or more homology.

The present invention also includes DNA which hybridises to the DNA of the present invention. Preferably such hybridisation occurs at, or between, low and high stringency conditions. In general terms, low stringency conditions can be defined as 3×SCC at about ambient temperature to about 65° C., and high stringency conditions as 0.1×SSC at about 65° C. SSC is the name of a buffer of 0.15M NaCl, 0.015M trisodium citrate. 3×SSC is three times as strong as SSC and so on.

The present invention further includes DNA which is degenerate as a result of the genetic code to the DNA of the present invention.

According to another aspect of the present invention there is provided a polypeptide which is an insect toxin and which is substantially free from other proteins with which it is ordinarily associated, and which is coded for by any of the DNA of the present invention, including derivatives thereof.

According to yet another aspect of the present invention there is provided a polypeptide having the amino acid sequence of any one of Sequence ID Nos. 20, 47, 58 or 37, including derivatives thereof.

Preferably said amino acid derivative is a homologous variant, preferably having 80% or more common amino acids, more preferably 90% or more common amino acids. Preferably any changes are conservative amino acid changes. By conservative amino acid changes we mean replacing an amino acid from one of the amino acid groups, namely hydrophobic, polar, acidic or basic, with an amino acid from within the same group. An example of such a change is the replacement of valine by methionine and vice versa.

The present invention also includes polypeptides which are translated from mRNAs arising from alternative splicing pathways for the primary transcription products derived from each of the cognate genes. The present invention further includes polypeptides which are produced by post-translational modification of the polypeptides of the present invention. Such post-translational modifications include peptide cleavage, addition of prosthetic groups, glycosylation or formation of multisubunit structures.

The cDNAs of the present invention code for polypeptides which form the insect toxin of the present invention. The polypeptides of the present invention correspond to the subunits of the insect toxin of the present invention.

In addition, each cDNA sequence of the present invention codes for a polypeptide which individually may provide an effect which is toxic to insects. Each of the polypeptides of the present invention may therefore provide an effect which is toxic to insects.

According to further aspect of the present invention there is provided a recombinant DNA construct comprising a DNA sequence of the present invention. Such constructs include cloning vectors such as plasmids and phages suitable for transforming a cell of interest. According to another aspect of the present invention the recombinant DNA construct is an expression vector. The present invention includes any suitable constructs which are, or become, available. According to a yet further aspect of the present invention there is provided a transformed system comprising the recombinant construct of the present invention. Such systems include mammalian cells, non-mammalian vertebrate and invertebrate cells, insect cells, and plant cells. The present invention also include bacteria, yeast, particularly fungi, and transformed with the recombinant constructs of the present invention, and viruses whose genomes have been directly or indirectly genetically manipulated to enable them to incorporate the DNA of the present invention. Suitable systems for transformation/genetic manipulation will be known to those skilled in the art. The method for producing such recombinant constructs/systems is not particularly germane to the present invention and any method suitable for the target may be used; such methods are known in the art.

The DNA/toxins/polypeptides of the present invention are obtainable from a parasitic wasp, such as from the superfamily Ichneumonidea. Preferably the toxin is obtainable from the family Braconidae. Examples of the family Braconidae are in the genera Apanteles, Bracon, Microbracon and Stenobracon.

In an especially preferred embodiment the DNA/toxin/polypeptide is obtained from *Bracon hebetor*.

The DNA/toxins/polypeptides of the present invention may be obtained from other sources/via different routes, for example using conventional cloning techniques or synthetic methods.

In a further aspect of the present invention there is provided a biological control agent comprising an insect toxin, polypeptide, recombinant DNA construct, or transformed system of the present invention. In this case the biological control agent preferably further includes an agronomically acceptable solid or liquid carrier. There is therefore provided a method of combating an insect pest in a habitat which comprises treating the pest or habitat with a pest-controlling effective amount of an insect toxin of the present invention. The present invention also includes biological control agents having a genome comprising nucleic acid of the present invention under the control of a promoter sequence which enables expression of said nucleic acid. Therefore included within the term biological control agent are viral, prokaryotic or eukaryotic organisms which when brought into association with an insect are capable of infecting the insect and interfering with the normal biochemical, physiological or electrophysiological processes and ultimately leading to the death of the insect. Suitable biological control agents within the scope of the invention include those based on bacterial, viral and fungal pathogens of insects. Bacterial pathogens include for example Bacillus species such as *B. thuringiensis, B. cereus* and the like. Fungal pathogens of insects include for example Beauvaria species such as *B. bassiana*.

Alternatively the biological control agent can be a genetically modified plant endophyte in which the genome has been altered to incorporate at least one nucleic acid sequence of the present invention. When such an endophyte is brought into association with a plant the toxin coded for by the nucleic acid may be expressed by the endophyte within the plant and exert toxic effects on insects feeding on or dwelling within the plant.

In a further variation the biological control agents can be a plant itself, particularly a crop plant being grown for food of fibre products, in which the plant genome has been modified by incorporation of at least one nucleic acid sequence of the present invention.

Various preferred features and embodiments of the present invention will now be described by way of non-limiting example with reference to the accompanying drawings in which:

FIG. 3 shows the results of size-fractionation chromatography of B-1;

FIG. 4 shows a graph used to calculate the molecular weight of the native B-1 toxin;

FIG. 6 shows the N-terminal amino acid sequence information for the subunits obtained from BrhTX-1;

FIG. 7 shows the N-terminal amino acid sequence for subunit BrhTX-1(a) and the corresponding degenerate oligonucleotide design of BH(a)A, BH(a)B and BH(a)I;

FIG. 8 shows the cDNA sequence of subunit BrhTX-1(a) and the deduced amino acid sequence;

FIG. 9 shows the N-terminal amino acid sequence for subunit BrhTX-1(d) and the corresponding degenerate oligonucleotide design of BH(d)A, BH(d)B and BH(a)I;

FIG. 10 shows the cDNA sequence of subunit BrhTX-1 (d) and the deduced amino acid sequence;

FIG. 11 shows the cDNA sequence and deduced amino acid sequence of the insert of pBrhTX-1(b)1, in which the primer sequences, BH(b)C and BH(b)D are indicated in bold text, and the 5'-3' direction indicated by arrow heads;

FIG. 12 shows the putative cDNA sequence of subunit BrhTX-1(b) from plasmid pBrhTX-1(b)6 and the deduced amino acid sequence;

FIG. 13 shows the protein translation of the putative cDNA of subunit BrhTX-1(b) with the mature peptide is shown underlined;

FIG. 14 shows the concensus cDNA sequence of subunit BrhTX-1(b) and the deduced amino acid sequence;

FIG. 15 shows peptide fragments from subunit BrhTX-1(c) and their presumptive coding sequence;

FIG. 16 shows the sequence of the subunit BrhTX-1(c) PCR amplification product obtained using the primers BH(c)A and BH(c)B;

FIG. 17 shows the cDNA sequence of the subunit BrhTX-1(c) and the deduced amino acid sequence.

EXAMPLE 1

Figure 1:
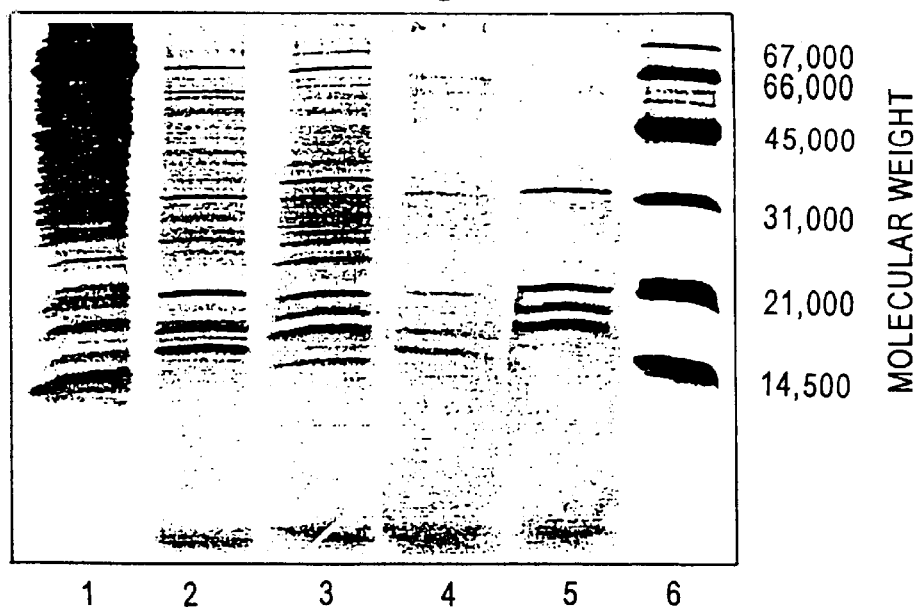
FIG. 1 shows an SDS-PAGE analysis of the separation of venom gland extracts B-1 and B-2 and the purified toxins BrhTX-1 and BrhTX-2.

Isolation and Characterisation of BrhTX-1 and BrhTX-2

Materials and Methods (i) Insects

An established population of *B. hebetor* (obtained from Dr R T Arbogast, USDA-ARS, P.O. Box 22909, Savannah, Ga., USA) was reared on larvae of the Indian meal-moth (*Plodia interpunctella*) at 25° C. with a photo-period of 16 hours light: 8 hours dark. Larvae of *P. interpunctella* and *G. mellonella* were obtained from an established population at the Commonwealth Scientific and Industrial Research Corporation, Division of Entomology, and raised at 25° C. on a diet, for *G. mellonella*, composed of 600 g rice flour infant cereal, 60 g brewer's yeast, 125 ml honey and 125 ml glycerol and, for *P. interpunctella*, composed of 1000 g soyflour, 500 g bran, 250 g dried yeast, 250 g wheatgerm, 500 g cracked wheat, 500 g rolled oats and 375 g glycerol.

(ii) Biological Assays for Toxin Activity

Paralysing activity in *B. hebetor* protein preparations was routinely determined using larvae of *G. mellonella*. The age and development status of the larvae used in bioassays was not determined; however, only larvae weighing between 0.15 g and 0.2 g were used. Biological assays were performed by injecting 10 μl of the protein sample, or control buffer, to be used between the prolegs into the haemocoel. Paralysis was scored if larvae did not move unless provoked and were unable to right themselves within 30 seconds after being placed on their back. Accurate monitoring of the toxin was facilitated by using end-point assays in which serial dilutions of a test extract were assayed for activity. Paralysing activity was measured using a modification of the Galleria Unit (GU) (Drenth (1974) *Toxicon*, 12, 198–192). The number of GUs in 10 μl of an injected extract was determined by taking the reciprocal of the extract dilution resulting in paralysis of larvae at approximately 2 hours post-injection. This value was then multiplied by 100 to obtain the number of GUs/ml extract.

(iii) Extraction of Venom Gland Components

Female wasps were anaesthetised at 4° C. and then kept on ice whilst their venom glands extracted by gently pulling on the ovipositor with fine forceps. Lots of 50 venom glands were extracted into 50 μl of iso-osmotic Pringle's saline (9 g/l NaCl, 0.2 g/l KCl, 0.2 g/l $CaCl_2$, 4 g/l dextrose) made 0.02% with sodium azide and containing the proteinase inhibitors EDTA (ethylenediamine tetraacetic acid, disodium salt) (5 mM), aprotinin (5 mM), and pepstatin (0.1 μg/ml). The proteinase inhibitors were obtained from Boerhringer-Mannheim. The glands were homogenised by hand using a microhomogeniser and insoluble material was pelleted by centrifugation at 14,000 rpm for 5 minutes in an Eppendorf microfuge. The supernatant containing the toxin was then filtered through a 0.22 μm ultrafree-mC filter (Millipore, Bedford, Mass.).

(iv) Protein Determinations and Concentration

Protein content was determined with a protein assay kit obtained from Bio-Rad Laboratories using bovine serum albumin as standard. Protein samples were concentrated using Ultrafree-MC concentrating units (Millipore) following the manufacturer's recommendations.

(v) Polyacrylamide Gel Electrophoresis and Anion Exchange Chromatography

Polyacrylamide gel electrophoresis (hereinafter PAGE) equipment and reagents, PAGE and gel filtration standard protein mixes, and silver staining reagents were all purchased from Bio-Rad Laboratories.

Denaturing SDS-polyacrylamide gel electrophoresis was performed as described by Laemmli (1970) *Nature*, 222, 680–685 using a 15% slab gel (11 cm×14 cm×0.075 cm) with a 4% stacking gel. Protein samples were made with 0.125 mM Tris-HCl [pH 6.8], 10% glycerol, 10% SDS (sodium dodecyl sulphate), 0.25% β-mercaptoethanol, 0.025% bromophenol blue, and heated at 95–100° C. for 5 minutes before loading onto the gel. Proteins were fractionated at 200 volts until the bromophenol blue tracking dye reached the base of the gel (approximately 45 minutes). Proteins were detected by staining with either Coomassie Blue stain (obtained from Gradipore) for 2 hours followed by destaining in distilled water overnight or with silver stain.

The molecular weights of the proteins were estimated by comparison with the molecular weights of the following standard proteins: rabbit muscle phosphorylase b (97,400 Da); bovine serum albumin (66,200 Da); ovalbumin (45,000 Da); bovine carbonic anhydrous (31,000 Da); soybean trypsin inhibitor (21,500 Da); lysozyme (14,400 Da).

Non-denaturing native PAGE was carried out on 7.5% polyacrylamide slab gels (11 cm×14 cm×0.075 cm) with 4% stacking gels. Native gels were prepared in the same manner as the SDS-PAGE gels with the exception that SDS was not added to the gel or to the running buffers. Samples were made in 0.125 mM Tris-HCl [pH6.8], 10% glycerol, and were not heated before loading onto the gel. Electrophoresis was carried out at 200 volts for 1.5 hours at 4° C.

Initial separation of soluble venom gland proteins was achieved using native-PAGE. Extracts of 600 venom glands were loaded onto each gel. Following electrophoresis the gels were horizontally sectioned into 4 mm strips and proteins were passively eluted from the gel slices with gentle shaking in 600 μl of 50 mM Tris-HCl [pH 8.0] for 16 hours at 4° C. An aliquot of each eluant was diluted 50-fold with 50 mM Tris-HCl [pH 8.0] and assayed for paralysing activity in G. mellonella as described above.

Paralysing activity was further purified over an anion exchange column, namely Mini Q (PC, 3.2 mm×3 cm, Pharmacia) using the SMART chromatography system (Pharmacia). Native-PAGE eluants containing paralysing activity were passed through 0.22 μm filters (Millipore) before loading onto the column. The column was equilibrated with 50 mM Tris-HCl [pH 8.0] and proteins were eluted at a flow rate of 200 μl/min using a linear gradient of 0 to 1 M NaCl. Proteins eluted from the column were detected by monitoring the absorbance of the eluant at 280 nm. Fractions of 200 μl were collected and assayed for paralysing activity. Fractions with paralysing activity were further analysed by SDS-PAGE.

(vi) Gel-filtration Chromatography

To estimate the molecular mass of the native paralysing toxin, 50 μl of native-PAGE eluants containing paralysing activity were applied to a gel-filtration column, namely Superose 12 (PC, 3.2 mm×30 cm, Pharmacia) that had been previously calibrated with the following standard proteins: thyroglobulin (670,000 Da); gamma globulin (158,000 Da); ovalbumin (44,400 Da); myoglobin (17,000 Da); vitamin B12 (1,350 Da). The column was pre-equilibrated with 50 mM Tris-HCl [pH 8.0], 150 mM NaCl and the protein eluted in the same buffer at a flow rate of 40 μl/min. Protein eluted from the column was detected by monitoring the absorbance of the eluant at 280 nm. Fractions of 40 μl were collected and diluted 20-fold with 50 mM Tris-HCl [pH 8.0] before being assayed for paralysing activity.

Results (i) Selection of Starting Material

Due to the small size of the adult *B hebetor* (2–3 mm) and the corresponding minute size of the venom gland, we initially examined whether whole wasps or isolated venom glands would provide the most appropriate starting material for isolation of the neurotoxin. Three preparations of 25 whole females or isolated venom glands were analysed for protein content and paralysing activity (GUs). The results show that both preparations possess comparable toxic activity (approximately 25,000 GUs) but that extracts of whole female wasps have a 10-fold higher concentration of soluble protein than extracts of isolated venom glands as shown below in Table 1. This demonstrates two important points: observed neurotoxic activity is associated with soluble venom glands components; and venom gland extracts provide a 10-fold enrichment of neurotoxin. Glands were used as the starting material for the purification of the neurotoxin.

TABLE 1[a]

| Extract | Toxin Units (GUs) (×1000) | Protein (mg) | Specific Activity (GU/mg × 1000) |
|---|---|---|---|
| Homogenised venom gland | 25 ± 5 | 0.100 ± 0.007 | 252 ± 55 |
| Whole female wasp | 25 ± 12 | 0.98 ± 0.2 | 24 ± 8 |

[a]Values are the result (± standard deviation) of 3 lots of preparations each of 25 wasps or venom glands.

(ii) Polyacrylamide Gel Electrophoresis and Anion Exchange Chromatography

Soluble venom gland extracts were first separated by native-PAGE. Following electrophoresis the gel was sectioned horizontally into 4 mm slices and each slice placed in buffer to recover the proteins by passive elution. Neurotoxic activity was generally quite diffuse and found in a large portion of the gel. However, end-point analysis revealed that after a 2 hour electrophoresis time activity was predominantly located in the first 2–3 cm of the gel. Toxin recovered from this region of the gel was subsequently termed B-1. Toxic activity did not migrate significantly further even after extended electrophoresis times of 3–4 hours. Larvae of *G. mellonella* injected with recovered toxin showed intoxication symptoms consistent with neuromuscular paralysis. No skeletal muscle activity was observed; however, mouth parts were visibly active and excreta was released. Occasionally, a second paralysing activity, subsequently termed B-2, was observed which migrated slightly faster than B-1. Since the two activities were often found in non-adjacent gel slices and could be completely resolved, they were considered to be distinct and separate activities.

Native-PAGE fractionation provided a 90-fold enrichment of B-1 neurotoxic activity from whole wasps, as shown below in Table 2, and an overall recovery of toxic activity of 41%.

TABLE 2[a]

| Purification step | Protein (μg) | Toxic Activity (GU × 10³) | Specific Activity (GU/μg protein) | Recovery (%) | Purification (-fold) |
|---|---|---|---|---|---|
| Venom gland extract | 772 ± 3[b] | 203 ± 46 | 263 | 100 | 10[c] |
| Native PAGE | 37 ± 9 | 84 ± 34 | 2,270 | 41 | 86 |
| Anion exchange | 4 | 13 | 3,333 | 7 | 127 |

[a]Values were obtained from 3 different lots of 300 venom glands separated using native-PAGE. Native-PAGE preparations were then pooled for anion exchange chromatography and the protein and toxin unit values divided by 3 for the purpose of comparison.
[b]Mean ± standard error of the mean
[c]Value based on comparison between whole female wasp and venom gland extract (see Table 1).

The separation of venom gland extracts, B-1 and B-2 using SDS-PAGE is shown in FIG. 1. In FIG. 1, Lane 1 corresponds to venom gland extract; Lane 2 to Native-PAGE purified B-1; Lane 3 to Native-Page purified B-2; Lane 4 to anion exchange purified BrhTX-1 (approximately 1 μg); Lane 5 to anion exchange purified BrhTX-2 (approximately 3 μg); and Lane 6 to molecular weight markers. Although the protein profile is still complex, specific enrichment of polypeptide bands with molecular weights of approximately 22,000 Da, 18,000 Da, 17,000 Da and 16,000 Da is seen.

Figure 2:
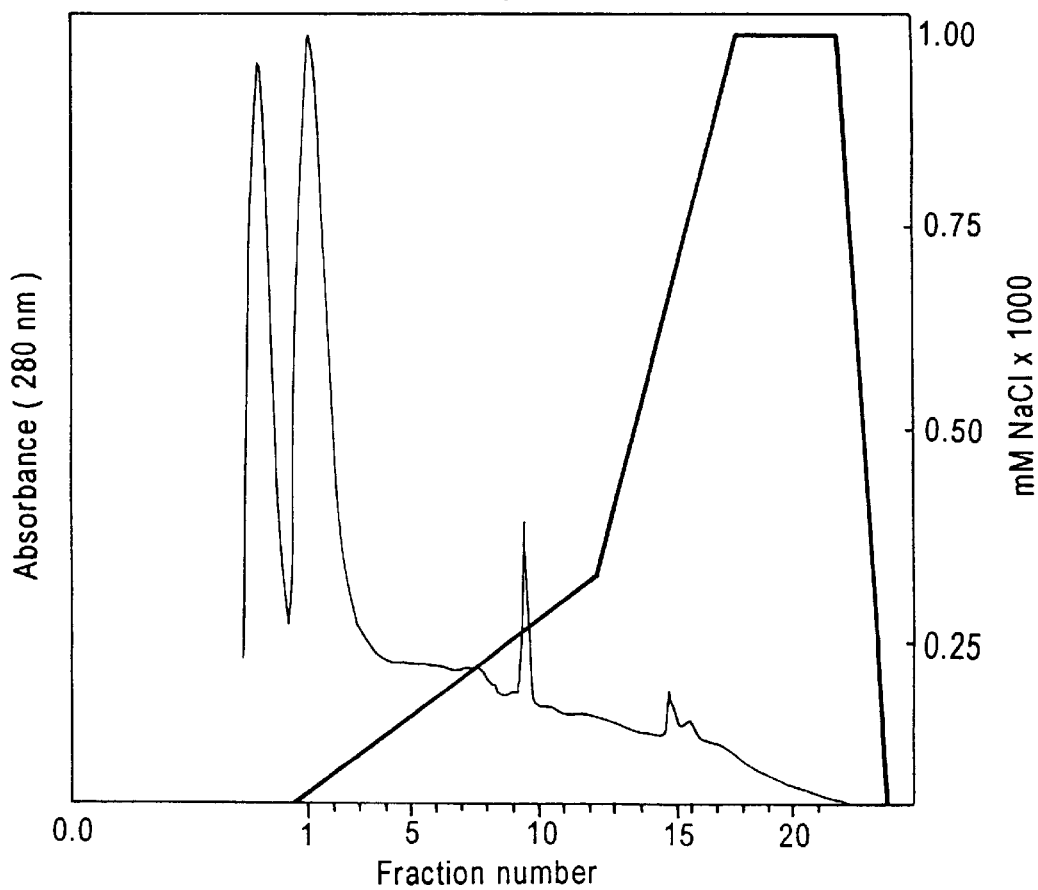
FIG. 2 shows the results when extract recovered using non-denaturing PAGE is further separated using anion-exchange chromatography.

In a final purification step, B-1 and B-2 were further fractionated using anion-exchange chromatography. When passed separately over the column, each activity eluted at approximately 200 mM NaCl and was confined to a single fraction that correlated with one distinct chromatographic peak as shown in FIG. 2 for B-1, which shows the chromatograph for native-PAGE eluants (400 μl) containing B-1 loaded onto the column. All paralysing activity was found in fraction No. 9. Biological assay of collected fractions revealed that all measurable paralysing activity of both B-1 and B-2 was present in this single fraction. The combination of native-PAGE and anion-exchange chromatography purified B-1 activity 126-fold from whole wasps with an overall recovery of 7% of starting toxic activity. Analysis of anion-exchange purified B-1 and B-2 using SDS-PAGE under reducing conditions shows that both activities appear similar and both resolve into four polypeptides, hereinafter referred to as subunits BrhTX-1(a), BrhTX-1(b), BrhTX-1(c) and BrhTX-1(d) for B-1, and subunits BrhTX-2(e), BrhTX-2(f), BrhTX-2(g) and BrhTX-2(h) for B-2. The purified toxins were named bracon toxin-1 (BrhTX-1) and bracon toxin-2 (BrhTX-2). At this stage of the purification BrhTX-1 corresponded to approximately 0.5% of the soluble protein from venom gland extracts. More particularly, these techniques indicate that the polypeptides BrhTX-1(a), BrhTX-1(b), BrhTX-1(c) and BrhTX-1(d) of BrhTX-1 have estimated molecular weights of 15,000 Da, 17,000 Da, 21,000 Da and 34,000 Da respectively. The polypeptides BrhTX-2 (e), BrhTX-2(f), BrhTX-2(g) and BrhTX-2(h) of BrhTX-2 have estimated molecular weights of 17,000 Da, 18,500 Da, 21,000 Da and 34,000 Da respectively.

(iii) Gel-Filtration Chromatography

The predicted molecular weight of BrhTX-1 and BrhTX-2 calculated from the four polypeptides resolved using SDS-PAGE is 87,000 Da and 90,500 Da respectively. In order to determine the native molecular mass of BrhTX-1 and BrhTX-2, native-PAGE fractions were separated on a Superose 12 gel-filtration column. The majority of toxic activity eluted in two fractions that corresponded to a single major peak on the chromatogram. The results for BrhTX-1 are shown in FIG. 3, which shows a size-fractionation chromatography of BrhTX-1; the hatched peak respresenting the fractions containing paralysing activity. Using a standard curve derived from the protein standards used to calibrate the column, the native toxin of BrhTX-1 was calculated to have a molecular weight of approximately 81,000 Da, as shown in FIG. 4. More particularly, a $K_{av}$ for each standard was calculated and plotted against the molecular weight of the protein. Using the $K_{av}$ for toxic activity and the slope and intercept of the regression line ($r^2=0.98$) for the standards, the molecular weight of the paralysing activity was calculated. BrhTX-2 was also calculated to be approximately 81,000 Da.

(iv) Analysis of the secondary structure of BrhTX-1

Figure 5:
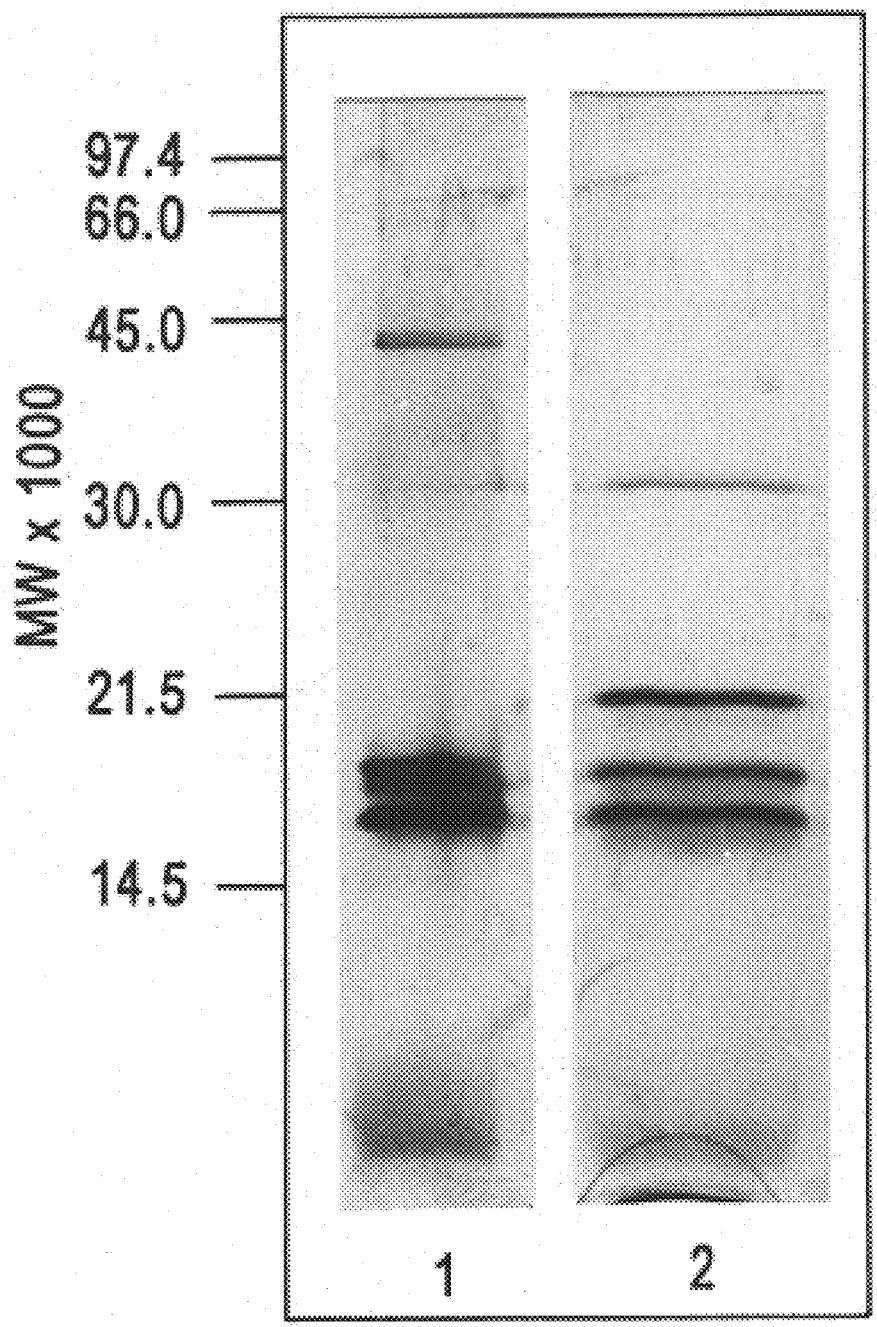
FIG. 5 shows the results of fractionation of BrhTX-1 using PAGE under reducing and non-reducing conditions.

The secondary structure of BrhTX-1 was investigated using SDS-PAGE under non-reducing and reducing conditions. The results are shown in FIG. 5, in which Lane 1 correspond to BrhTX-1 fractionated using SDS-PAGE in the absence of reducing agents; and Lane 2 corresponds to an identical sample run on Lane 1 that has been exposed to 3% β-mercaptoethanol. As show in FIG. 5, migration of the polypeptides (a) and (b) are not significantly effected by the presence or absence of reducing agent, although under non-reducing conditions the polypeptide (b) appears to be present as a doublet. In contrast, under non-reducing conditions, the polypeptides (c) and (d) are not visible and an apparent novel polypeptide of approximately 45,000 Da appears. Conversely, this band resolves into two polypeptides of 34,000 Da and 21,000 Da when re-fractionated using SDS-PAGE under reducing conditions (data not shown). This suggests that polypeptides (c) and (d) are cross linked with intra- or inter-molecular disulphide bonds. This is of particular interest since earlier studies such as Visser et al., (1983) *Comp. Biochem. Physiol.*, B75B, 523–538 have shown that *B. hebetor* paralysing activity is lost when venom is exposed to the reducing agents DTT and BME.

Discussion

Quantitative studies of extracts of 25 venom glands and 25 whole female wasps revealed that each contained, on average, 13,500 units of paralysing activity (GUs). This supports the assumption that the toxic activity identified in the *G. mellonella* bioassay is associated with soluble venom gland contents. To purify the paralysing agent, venom gland extracts where first fractionated using native-PAGE. Toxic activity did not migrate rapidly under the electrophoresis conditions used. Since native-PAGE separates by charge as well as size, this suggests that toxic activity has either an overall basic charge and/or a high molecular weight. The separation of two distinct activities (B-1 and B-2) that appear to differ in molecular weight by only 3,500 Da indicates that charge is the major contributing factor to the rate of the toxin's migration.

Anion-exchange chromatography of B-1 yielded a single protein. This purified preparation (BrhTX-1) represented 7% of the starting paralysing activity present in extracts of venom glands and presumably whole female wasps and 0.5% of soluble venom gland proteins. The overall enrichment of toxic activity is 127-fold and yields a preparation with a specific activity of 3,333 units of toxic activity per μg of protein.

The data reported here provide evidence that we have purified two oligomeric toxins, BrhTX-1 and BrhTX-2, which do not dissociate under native-PAGE or mild chromatographic conditions. Both toxins are composed of four polypeptides that can be separated using SDS-PAGE. Furthermore, separation of BrhTX-1 using SDS-PAGE under reducing and non-reducing conditions suggests that two of the subunits, BrhTX-1(c) and BrhTX-1(d), are held with a disulphide bond.

EXAMPLE 2

Sequence Analysis of BrhTX-1

(i) Protein Purification 45,000 glands were purified using native-PAGE and anion exchange chromatography on the SMART system to yield 300 μg of BrhTX-1. The toxin was essentially homogeneous when analysed using SDS-PAGE followed by silver staining and composed of four polypeptides—BrhTX-1(a), BrhTX-1(b), BrhTX-1(c) and BrhTX-1(d). The specific activity of the final preparation was 3,250,000 GUs/mg protein. Furthermore, with this data it can be estimated that 0.3 ng of purified toxin can completely paralyse *G. mellonella* larvae weighing 0.2 g.

The specific activity value also permits comparison of the toxin to the toxin from the straw-itch mite (*Pyemotes tritici*). The reported paralysis dose of the straw-itch mite toxin is 330–550 μg/kg *G. mellonella* larvae. BrhTX-1 has a paralysis dose of approximately 2 μg/kg *G. mellonella* larvae. BrhTX-1 was found to be very stable at 4° C., and even after several weeks over 90% of the activity was still present.

(ii) Sequence Analysis

Approximately 200 μg of BrhTX-1 toxin was separated into its subunits using SDS-PAGE followed by electrotransfer in 10 mM Caps (zwitterionic buffer) [pH 11.0]/10% methanol at 60 mAmps for 1 hour at room temperature. The separated subunits were electroblotted onto PVDF (polyvinylidine fluorine) membrane. Following the transfer the blot was washed in Milli-Q water for 1 hour and then dried under vacuum. Protein bands were visualised by staining for approximately 30 seconds in 0.0005% sulforhodamine B (obtainable from Sigma) in 30% methanol/0.2% acetic acid followed by destaining in water. Small amounts of toxin, about 10 μg, were initially used to optimise the blotting conditions after which 150 μg of toxin was prepared for sequence analysis.

Sequencing was carried out using an ABI 477A protein sequencing system (from Applied Biosystems). Problems were encountered during the sequencing of BrhTX-1(a), BrhTX-1(b) and BrhTX-1(c); notably, after 2 or 3 cycles, a clearly detectable signal from the amino acid analyser would disappear, indicating that much of the protein was being removed from the membrane during the sequencing process. This problem was overcome by applying greater concentrations of protein to the membrane.

Amino-terminal sequence of all four subunits was obtained as shown in FIG. 6 (*indicates amino acid residues where there was some ambiguity in the identity of the amino acid sequence). This sequence information is also shown in Sequence ID No. 1 for subunit BrhTX-1(a); Sequence ID No. 2 for subunit BrhTX-1(b); Sequence ID No. 3 for subunit BrhTX-1(c); and Sequence ID No. 4 for subunit BrhTX-1(d).

(iii) Subunit Structure Studies

Toxic activity was found to be associated with a small polypeptide from BrhTX-1 of between 14,000 Da and 18,000 Da that had been isolated using native-PAGE containing Triton X-100. From such gels we recovered about 1,500 GUs from the total of about 30,000 that had been loaded. Although this represents only about 5% of the total activity loaded onto the gel, a substantial amount of the activity migrates only a small way into the gel. These results illustrate that the subunit has substantial activity.

(iv) Western Blot Analyses

Antibodies were generated against the BrhTX-1(a), BrhTX-1(c), BrhTX-1(d) subunits by utilising the N-terminal sequence FIG. 6 and Sequence ID Nos. 1,3 and 4 respectively) made available by the direct protein sequencing described above. These antibodies were generated commercially by Chiron Mimitopes (Clayton, Victoria) as outlined below.

Synthetic peptides were generated to match the available sequence and linked to a diphtheria toxin carrier. These conjugates were then used to immunise three separate New Zealand White rabbits. Rabbits were immunised intramuscularly with 0.39 mg of the peptide in Freund's Complete Adjuvent.

After completion of the first immunisation, the rabbits were exsanguinated from an ear vein using a cannula and then exsanguinated again at days 14, 35 and 42. Serum was prepared by incubating the blood at 37° C. for 30 minutes and then chilling on ice for 15 hours prior to removal of cellular material by low-speed centrifugation. The serum was stored at −20° C.

All crude antisera were titrated in ELISA against a biotinylated derivative of the immunising peptide, diphtheria toxin and avidin. In these titration experiments the ELISA plate was coated with avidin, to which the biotinylated peptide and the antibody being tested were sequentially bound. Quantification of the antibody was then achieved using an anti-rabbit IgG serum linked to horseradish peroxidase. Using the highest titred sera against each of the subunits, Western blots were carried out against purified BrhTX-1 separated into its constituent subunits by SDS-PAGE as previously described. After electrophoresis proteins were transferred to nitrocellulose (Biorad, Hercules, Calif.).

Using 10 μl of purified BrhTX-1 (approximately (8 μg), separated by SDS-PAGE, a specific reaction was obtained against the relevant subunit of all three sera tested.

(v) Peptide/Digestion Sequencing

Approximately 800 μg of BrhTX-1 was separated into its consistuent subunits by SDS-PAGE as previously described. After electrophoresis the subunits were visualised in the gel by staining with Coomassie Brilliant Blue. Bands corresponding to each of the subunits were then excised from the gel and the SDS eluted from the gel by washing twice in buffer containing 0.2M ammonium bicarbonate, 0.02% Tween-20. Then 0.5 μg of sequencing grade trypsin (Promega, Madison, Wis.) was added and the gel fully rehydrated by the addition of approximately 20 μl of 0.2M ammonium bicarbonate. The gel slice was then transferred into a microfuge tube and covered with 0.2M ammonium bicarbonate, 0.02% Tween-20 and incubated at 30° C. overnight. The reaction was stopped by the addition of one tenth volume of 10% w/v trifluoroacetic acid.

After digestion, the resulting peptides were eluted from the gel by extraction for 40 minutes in 100 μl of 0.1% w/v trifluoroacetic acid in 60% acetonitrile at 30° C. The resultant supernatant was then reduced to a final volume of 20 μl by rotary evaporation (Hetovac (Heto) Scandinavia).

The peptides were then separated by reverse phase chromatography on a SMART system using a μRPC C2/C18 SC2.1 1/10 column. Gradients over this column were formed by using the buffers 0.065% trifluoroacetic acid and 0.05% trifluoroacetic acid in 40% acetonitrile. Fractions were collected using the "Peak Fractionation" function.

Individual peaks from this chromatography step were then subjected to mass spectroscopy (Tofspec, Fisons Instruments) to ascertain the size of the recovered peptides. Peaks were then sequenced using a Procise-HT sequencer (Applied Biosystems). A summary of the tryptic fragment sequence obtained from the subunits of BrhTX-1 is given below in Table 3.

TABLE 3

| Subunit | Total Number of Fragments Sequenced | Sequences Obtained[1] |
| --- | --- | --- |
| BrhTX-1(d) | 5 | INI(Q/R)VA |
| | | QIVTYYLDS(I/H)K |
| BrhTX-1(c) | 6 | GIAQDVGHAAHSFTK |
| | | (H/G)VHNPGNFR |
| BrhTX-1(b) | 5 | MIKPGETYGDVTNK |
| | | EWVHDNAGTLLPR |
| | | DVHDNAGTLLPR |
| | | PHTVYDKHESLQ |
| BrhTX-1(a) | 4 | FNPETHR |
| | | EAYIQNHGA |

[1]Where there were ambiguities in the sequence obtained the possible options are shown in brackets separated by a slash (/).

EXAMPLE 3

Cloning of Subunits of BrhTX-1

Generation of cDNA Library and Library Plating

Total RNA was isolated from newly emerged female B. hebetor, which had been frozen in liquid nitrogen and stored at −70° C. To isolate total RNA, approximately 1 g of frozen wasps were ground to powder in liquid nitrogen. The powder was further homogenised in a hand-held homogeniser in 20 ml of 8M guanidinium chloride. Large fragments of insoluble material were removed by centrifugation at 10,000×g for 10 minutes and total RNA was precipitated in the presence of 32% v/v ethanol. Subsequent purification of the total RNA was then carried out as described in Sambrook et al., (1989) *Molecular Cloning: A Laboratory Manual*, Cold Spring Habor Press.

mRNA was isolated from total RNA using oligo (dT)-cellulose spin columns obtained from Pharmacia Biotech (Uppsala, Sweden) as per the manufacturer's instructions. Approximately 5 μg of mRNA was used for the cDNA synthesis. Eco RI/Not I linkers were ligated onto the blunt ended double stranded cDNA, ligated into Eco RI digested λgt 11 DNA, and transformed into commercially available *E coli* Y1090, and subsequently amplified using standard techniques. Titring was carried out prior to screening of the library by standard methods (Sambrook 1989) using plating cells prepared from the commercially available *E coli* LE392 strain. The titre of the library was 1.25×10⁹ pfu/ml.

For screening 500,000 pfu were plated-out on ten 140 mm Petri dishes with approximately 50,000 plaques per plate. Plaque lifts were done in triplicate on to Hybond-N membranes (Amersham International) using standard methods (Sambrook 1989).

EXAMPLE 4

Cloning of Subunit (a) of BrhTX-1

(i) Generation of Probes

Three pools of degenerate oligonucleotides, designated BH(a)A, BH(a)B and BH(a)I, which code for at least part of the N-terminal sequence of BrhTX-1(a), were designed. Inosines, represented by "I", were used where there was full degeneracy. These oligonucleotides are shown in FIG. 7 and also Sequence ID Nos. 5, 6 and 7 (where isosine is represented by "N"). The oligonucleotides were synthesised by standard methods on an Applied Biosysterns 380B DNA synthesiser. Each oligonucleotide was deprotected for 16 hours at 55° C. then divided into three screw-cap polypropylene microcentrifuge tubes and dried-down under vacuum. One third of each oligonucleotide was dissolved in 100 μl $H_2O$ and quantified by UV spectroscopy, 1 $OD_{260}$/ml equivalent to 25 μg/ml.

(ii) Screening of library and Isolation of Clones

Each set of filters was probed with one of the oligonucleotides, either BH(a)A, BH(a)B or BH(a)I. 25 ng of each oligonucleotide was labelled by 5' phosphorylation with $^{32}$P-ATP (Amersham International) and T4 polynucleotide kinase (Northumbria Biologicals Ltd) using standard methods (Sambrook 1989). Incubation was 30 minutes at 37° C. Filters were prehybridised for 2 hours at 45° C. in 5×SSPE (20×SSPE: 3.6 M NaCl, 0.2 M $NaH_2PO_4$, 0.02 M EDTA [pH7.7]), 5×Denhardt's Reagent [50×Denhardt's Reagent: 5 g Ficoll (Type 400, Pharmacia), 5 g polyvinylpyrrolidone, 5 g bovine serum albumin (Fraction V, Sigma)], 0.5% SDS and 200 μg/ml salmon sperm DNA. Hybridisation was carried-out in 5×SSPE, 5×Denhardt's Reagent, 0.5% SDS plus labelled probe at 45° C. for 16 hours.

Filters were washed in 6×SSC, 0.1% SDS at 45° C. for 4×15 minutes and then exposed to Kodak X-AR film, with intensifying screens, at −80° C.

Three plaques hybridised to both BH(a)A and BH(a)I, one plaque hybridised to both BH(a)B and BH(a)I. No plaques hybridised to all three probes. After three subsequent rounds of plaque purification, three of the four plaques had been purified to homogeneity and continued to display hybridisation to BH(a)I. Phage plaques were picked into 1 ml SM buffer (50 mM Tris-HCl [pH7.5], 0.1 M NaCl, 0.2% (w/v) $MgSO_4.7H_2O$, 0.01% (w/v) gelatin) plus 10 μl chloroform.

(iii) Characterisation of Clones

The plaque-purified phage were screened for the presence and size of a cDNA insert by polymerase chain reaction (hereinafter PCR) analysis. Two oligonucleotides, λgt 11 forward and λgt 11 reverse, were used, as shown below and in Sequence ID Nos. 8 and 9 respectively. These oligonucleotides are specific for λgt 11 and flank the Eco RI cloning site.

λgt 11 forward 5'-GACTCCTGGAGCCCG-3'

λgt 11 reverse 5'-TTGACACCAGACCAACTGGTAATG-3'

The PCR reactions were carried out in 0.5 ml polypropylene microcentrifuge tubes using 25 mole of each concentrated primer, 0.5 μl phage stock, 8 μl Ultrapure dNTPs (Pharmacia) 1.23 mM of each, 2.5 μl 500 mM KCl, 100 mM Tris [pH8.4], 15 mM $MgCl_2$, 0.1% (w/v) gelatin and 0.2 μl (1U) Taq DNA polymerase (Perkin/Elmer Cetus). One drop of light mineral oil (Sigma) was added. The tubes were placed in a Techne PHC-1 Programmable Dri-block and subjected to the following temperature regime:

5 seconds at 94° C.;

1 second at 94° C.; 2 seconds at 40° C.; 3 seconds at 72° C. (35 cycles) followed by a final incubation period of 7 seconds at 72° C.

10 μl of each reaction was analysed by agarose gel electrophoresis. All 3 phage stocks generated a PCR amplification fragment which indicated the following cDNA insert sizes:

λBrhTX-1(a)1.1—about 600 base pairs (bp);

λarhTX-1(a)1.2—about 620 bp; and

λBrhTX-1(a)1.3—about 590 bp.

(iv) Subcloning and Sequencing of Clones

Phage DNA preparations were carried-out using the method of Grossberger D (1987) *Nucleic Acid Research,* 15(10), 6737. The cDNA inserts were released from λBrhTX-1 (a)1.1 and λBrhTX-1 (a)1.2 by Eco RI digestion. The insert from λBrhTX-1 (a)1.3 was not released which probably indicates that the Eco RI sites had not been recreated during the original library construction. The two released inserts were each ligated into Eco RI digested, phosphatase treated plasmid pUC19 with T4 DNA ligase in appropriate buffer conditions (Sambrook 1989). The ligation mixtures were used to transform competent commercially available *E coli* DH5α cells under standard conditions (Sambrook 1989). Transformants, designated pBrhTX-1(a) 1.1 and pBrhTX-1(a)1.2, were selected on LB agar plates containing 100 μg/ml ampicillin.

The insert of clone pBrhTX-1(a)1.1 was sequenced using a Sequenase kit (USB, Cleveland, Ohio) and nine synthetic oligo primers, as shown below and in Sequence ID Nos. 10 to 18.

```
PUC4      5'-GCTGATGTGCTGCAAGGCGATFAAG-3'
PUC1      5'-TTCACAGAGGAAACAGCTATGAC-3'

BH(a)F1   5'-TCGTGAAGTGAAGAATTA-3'

BH(a)F2   5'-AATGTGTITGCACTCACG-3'

BH(a)F3   5'-CATATACAGCGAAGTACC-3'

BH(a)F4   5'-TTATATGAAGTTCTTAGA-3'

BH(a)R1   5'-GGCGCAATAATTCTTCAC-3'

BH(a)R2   5'-TAACTATGGGATTCTTAG-3'

BH(a)R3   5'-ATATTTAAAGCCTCCCGC-3'
```

Two of the primers, PUC4 and PUC1, hybridise to the regions of pUC 19 flanking the mcs. The other primers were designed using the sequence data generated by the initial PUC4 and PUC1 sequencing runs. The nucleotide sequence obtained is shown in Sequence ID No. 19. Translation of the nucleotide sequence gave an open reading frame (hereinafter ORF) of 125 amino acids. This deduced amino acid sequence is given in Sequence ID No. 20. Amino acids 17–36 correspond to the N-terminal sequence of subunit (a) as shown in Sequence ID No 1. Amino acids 1 to 16 have the features of a signal sequence for protein export. This nucleic acid sequence and corresponding amino acid sequence is also shown in FIG. 8.

(v) Analysis of Clones
Peptide Digestion/Sequencing The alignment of the sequences obtained using the peptide digestion method against the deduced amino acid translations from the cDNA is shown below:

| Peptide Sequence | FNPETHR |
|---|---|
| cDNA Sequence | FNPETHR |
| Peptide Sequence | EAYIQNHGA |
| cDNA Sequence | EACIQNHGA |

The apparent anomaly in the second alignment can be explained by the fact that detection of cysteine can be unreliable.

Genomic Southern Blot

Genomic DNA was prepared from male and female *B. hebetor* adults by the following method. Approximately 0.1 g of frozen wasps are gently homogenised in 500 μl of Lifton Solution (0.2M sucrose, 0.05M EDTA, 0.5M SDS, 0.1M Tris-HCl pH 9.0). When most of the material is broken up a further 500 μl of Lifton Solution is added and the homogenate is agitated until the tissue ceases to aggregate. The homogenate is then incubated at 65° C. for 30 minutes before the addition of 250 μl of 0.6M acetate. This solution is then gently mixed and left on ice for 1 hour. Large particulate matter is then removed by centrifugation at 4° C. in a bench-top centrifuge for 10 minutes at 10,000 rpm. The supernatant is then extracted sequentially with equal volumes of phenol (saturated with TE), phenol/chloroform:isoamyl alcohol (24:1) (IAC) and IAC. RNAse A is then added to a final concentration of 10 μg/ml and incubated at 37° C. for 15 minutes. Two volumes of ethanol are then added to the solution and the DNA precipitated by centrifugation at room temperature for 15 minutes at 8,000 rpm in a bench-top centrifuge. After washing the precipitated DNA with 80% ethanol and drying, the DNA is resuspended in 50 μl of TE and the concentration of DNA estimated spectrophotometrically.

The purified DNA was digested with the following restriction enzymes: Pst I, Bcl I, Acc I, and the fragments separated by electrophoresis in a 0.7% agarose gel in TAE buffer. DNA was blotted onto Hybond C+ (Amersham International) nitrocellulose membrane in a 20x2xSSC gradient and bonded to the membrane by baking at 80° C. for 4 hours. $^{32}$P-labelled cDNA probes were synthesised by PCR using the primers BH(a)R1 and BH(a)R3 and the plasmid clone pBrhTX-1(a)1.1 as target DNA. The probes were generated using the following PCR conditions: 5 minutes at 95° C.; then 30 seconds at 95° C.; 1.5 minutes at 45° C.; 1 minute at 72° C. (5 cycles); then 30 seconds at 95° C.; 1.5 minutes at 5° C.; 1 minute at 72° C. (5 cycles); then 5 minutes at 72° C.

Pre-hybridisation and hybridisation were carried out under the following conditions:

Pre-hybridisation—Two hours at 42° C. in pre-hybridising solution containing 6xSSC, 5xDenhardt's Reagent, 0.5% SDS, 50% formamide, 0.1% sodium pyrophosphate and 100 μg/ml salmon sperm DNA (sonicated and boiled prior to addition).

Hybridisation—overnight at 42° C. in pre-hybridising solution to which $^{32}$P-labelled probe had been added. The probe was boiled and then cooled rapidly on ice before addition to the filter and the pre-hybridising solution.

After hybridisation the filters were washed four times in 2xSSC, 0.1% SDS at 42° C. Each wash was carried out for 15 minutes. After washing the filters were blotted, wrapped in cling-film and exposed to Fuji medical film.

The results indicate only a single copy of the sequence is present in the genome: (1) a digest of the genomic DNA using Pst I gave a single hybridising fragment of about 3040 bp; (2) a digest using Bcl I gave a single hybridising fragment of 1400 bp (there is a Bcl I site present in the cDNA sequence immediately after the probe-hybridising sequence); and (3) a digest using Acc I gave two hybridising fragments that are consistent with the presence of an Acc I site at 357 bp in the cDNA sequence (see FIG. 8).

EXAMPLE 5

Cloning of subunit (d) of BrhTX-1

(i) Generation of Probes

Three pools of degenerate oligomers were designed, BH(d)A, BH(d)B and BH(d)I. Inosines were used were there was full degeneracy. These oligonucleotides are as shown in FIG. 9 and Sequence ID Nos. 21, 22 and 23. These oligonucleotides were synthesised by standard methods on an Applied Biosystems 380B DNA synthesiser. Each oligonucleotide was deprotected for 16 hours at 55° C. then divided into two screw-cap polypropylene microcentrifuge tubes and dried-down under vacuum. One half of each oligonucleotide was dissolved in 100 μl water and quantified by UV spectroscopy, 1 $OD_{260}$/ml equivalent to 25 μg/ml.

(ii) Screening of Library and Isolation of Clones

The library was screened using the protocol described above for subunit BrhTX-1(a).

Seven plaques hybridised to BH(d)I. After three subsequent rounds of plaque purification, six plaques had been purified to homogeneity and continued to display hybridisation to BH(d)I. Phage plaques were picked into 1 ml SM buffer and 10 μl chloroform.

(iii) Characterisation of Clones

The plaque-purified phage was screened and analysed using the protocol described above for subunit BrhTX-1(a).

Five of the six phage stocks generated a PCR amplification fragment which indicated the following cDNA insert sizes (replicas of the same original plaque are also listed):

λBrhTX-1(d)1.1—about 1200 bp; λBrhTX-1(d)1.2—about 1200 bp

λBrhTX-1(d)2.1—about 1200 bp

λBrhTX-1(d)3.1—about 1800 bp; λBrhTX-1(d)3.2—about 1800 bp; λBrhTX-1(d)3.3—about 1800 bp; λBrhTX-1(d)3.4—about 1800 bp λBrhTX-1(d)4.1—about 1200 bp; λBrhTX-1(d)4.2—about 1200 bp; λBrhTX-1(d)4.3—about 1200 bp λBrhTX-1(d)5.1—about 700 bp (iv) Subcloning and Sequencing of Clones As for subunit BrhTX-1(a), phage DNA preparations were carried out using the method of Grossberger D (1987). The cDNA inserts were released from λBrhTX-1(d)1.2, λBrhTX-1(d)3.1, λBrhTX-1(d)3.3, λBrhTX-1(d)3.4 and λBrhTX-1(d)4.3 by Eco RI digestion. The other inserts were not released which probably indicates that the Eco RI sites had not been recreated during the original library construction. The released inserts were cloned into the Eco RI site of pUC19 and then transformed into *E. coli* DH5α cells as described for subunit BrhTX-1(a).

The insert of clone pBrhTX-1(d)1.2 was sequenced as described for subunit BrhTX-1(a) using fourteen synthetic oligo primers including primers PUC4 and PUC1 (given above and in Sequence ID Nos. 10 and 11). The other twelve primers were designed using the sequence data generated by the initial PUC4 and PUC1 sequencing runs, and are shown below and in Sequence ID Nos. 24 to 35.

| | |
|---|---|
| BH(d)F1 | 5'-CTTCAAATTAGTGTACGA-3' |
| BH(d)F2 | 5'-TGTGGCAATGCACAGAAC-3' |
| BH(d)F3 | 5'-TCAAGATGCTAGATTGTC-3' |
| BH(d)F4 | 5'-TAATAAATGGTCATGATG-3' |
| BH(d)F5 | 5'-CGCTTTCAAATAGTCACT-3' |
| BH(d)R1 | 5'-ATTCACCATCTGAGCAAT-3' |
| BH(d)R2 | 5'-ACACAATTAGCCACTGTC-3' |
| BH(d)R3 | 5'-TTGTACTCAGAATGGACT-3' |
| BH(d)R4 | 5'-ATGTATGGAGCGATACCA-3' |

| | |
|---|---|
| BH(b)A | 5'-AC(TCA) TTG TT(TC) AC(TCA) GA(TC) CG(TC) AA-3' |
| BH(b)B | 5'-GG (ATG)CC (AG)AA (AGT)GT (TC)TT (AG)TC-3' |

-continued

| | |
|---|---|
| BH(d)R5 | 5'-ACATCATGAATTGCCTTG-3' |
| BH(d)R6 | 5'-TGTAAATGTGTAGTGGGT-3' |
| BH(d)R7 | 5'-GCGAGAAATTCACTATCA-3' |

The nucleotide sequence obtained is shown in Sequence ID No. 36. Translation of the nucleotide sequence gave an ORF of 275 amino acids. Amino acids 23–35 correspond to the N-terminal sequence of subunit BrhTX-1(d). Amino acids 1–22 comprise a candidate signal sequence. The estimated molecular weight of the mature protein encoded by the cDNA is 28.2 kDa. The deduced amino acid sequences are given in Sequence ID No 37. The nucleotide sequence and amino acid sequence is also shown in FIG. 10.
(v) Analysis of Clones
Peptide Digestion/Sequencing The protocol is as described above for subunit BrhTX-1 (a). The alignment of the sequences obtained against the deduced amino acid translations is shown below:

| Peptide Sequence | INI(Q/R)VA | QIVTYYLDS(I/H)K |
|---|---|---|
| cDNA Sequence | GNIK VA | QIVTYYLDW I K |

These mismatches can be ascribed to sequencing artefacts.
Genomic Southern Blot

Genomic DNA was prepared as previously described in Example 4. Aliquots of male and female DNA were digested using Bcl I, Nde I, Bgl II and Pst I and the digested DNA separated by electrophoresis in 0.7% agarose gels in TAE buffer. DNA was then blotted onto nitrocellulose membranes (HybondC+; Amersham UK) in a 2–20×SSC gradient and bonded to the membrane by baking at 80° C. for 4 hours.

$^{32}$P-labelled probes were synthesised by PCR using the primers BH(d)F4 and BH(d)R7 and pBrhTX-1(d)1.2 plasmid DNA as target DNA under the following conditions:
 5 minutes at 95° C.;
 30 seconds at 95° C.; 1.5 minutes at 43° C.; 1 minute at 82° C. (35 cycles); then
 5 minutes at 72° C.

Results for male and female DNA were identical. The Bcl I digest produced two hybridising fragments, one of 10.0 kbp and one of 9.1 kbp. This result was consistent with the presence of an Nde I site in the probe hybridisation region of the cDNA sequence. The Bgl II and Pst I digests produced single hybridising fragments of 18.5 kbp and 22.1 kbp respectively and are consistent with the absence of either of these sites in the probe hybridisng region of the cDNA.

EXAMPLE 6

Cloning of subunit (b) of BrhTX-1

(i) Generation of Probes

From the N-terminal sequence given in Sequence ID No. 2, two multi-species primers were designed. These probes are shown below and in Sequence ID Nos. 38 and 39.

These primers were used in a PCR experiment to generate a PCR product from cDNA synthesised from female mRNA as previously described. The PCR reaction conditions for a 0.2 μl Taq DNA Polymerase/50 μl reaction were as follows:
 5 minutes at 95° C.; then
 30 seconds at 95° C.; 1.5 minutes at 50° C.; 1 minute at 72° C. (5 cycles); then
 30 seconds at 95° C.; 1.5 minutes at 55° C.; 1 minute at 72° C. (30 cycles); then
 5 minutes at 72° C.

This PCR product is approximately 54 bp, as estimated by PAGE in 15% gels in TBE buffer. Amplification products were visualised in the gels by staining with ethidium bromide. The fragment was then cloned into the EcoRV site of the commercially available plasmid pBluescript SK- that had been tailed with a thymine residue (T-tailing) using Taq DNA Polymerase. The following conditions were used for T-tailing: 50 mM KCl, 10 mM Tris-HCl [pH 8.3], 1.5 mM MgCl$_2$, 2 mM dTTP at 70° C. for 2 hours. The cloned PCR product was sequenced using the following dye primers which are available from Applied Biosystems Inc: Universal M13–20 dye-primer: 5'-CAG GAA ACA GCT ATG ACC-3'M13 reverse dye-primer: 5'-TGT AAA ACG ACG GCC AGT-3'

Sequencing was carried out using an ABI 370 A DNA analysis system (Applied Biosystems). The sequence for the PCR product is given in Sequence ID No. 40, and below.
 5'-ACC TTG TTT ACA GAC CGC AAG TGG TGT GGA CGT GCC GAT AAG ACT TTC GGC CC-3'
(ii) Screening of library and Isolation of Clones Library plating was carried out as described above, except that plaque lifts were done in duplicate onto Nitropure nitrocellulose membranes, 137 mm 0.45 Micron, (Microb Separations, Westboro, Mass., USA). In the primary screen 3.6×10$^5$ plaques per filter (4 filters in total) were screened, in secondary and tertiary screens 100–250 plaques per filter were screened.

$^{32}$P-labelled probes were made by PCR. PCR was carried out in the presence of $^{32}$P-dATP using the oligonucleotides BH(b)A and BH(b)B shown in Sequence ID Nos. 38 and 39, and the cloned PCR product carrying the sequence shown in Sequence ID No. 40 as the target.

The following PCR conditions were used:

95° C. for 5 minutes prior to the addition of Taq polymerase; then

95° C. for 30 seconds, 45° C. for 1.5 minutes and 72° C. for 1 minute (5 cycles); then 95° C. for 30 seconds, 50° C. for 1.30 minutes and 72° C. for 1 minute (30 cycles); then 72° C. for 5 minutes (1 cycle).

Filters were probed with the $^{32}$P-labelled probe described above under the same pre-hybridising and hybridising conditions as described for the Genomic Southern Blot of subunit BrhTX-1(a). Ten plaques that hybridised to this probe were initially identified. Three of these were purified through second and third round screens to homogeneity. Plaque purified phage were picked into 1 ml of SM buffer plus 10 µl of chloroform.

(iii) Characterisation of Clones

The plaque-purified phage were screened for the presence and size of a cDNA insert by PCR analysis using the oligonucleotides λgt 11 forward and λgt 11 reverse. Lambda DNA for PCR was prepared from purified stocks by boiling 10 µl of the stock for 5 minutes. two µl of this DNA was then used in PCR experiments. The amplified fragments were sized by electrophoresis through 0.8% agarose gels in TAE buffer and sized against markers of known size. Of the three purified phage, an insert of approximately 500 bp was found in one phage, which phage was designated λBrhTX-1(b)1. No inserts could be detected in the other two plaque-purified phages.

(iv) Subcloning and Sequencing of Clones

Phage DNA was purified by isopyncnic centrifugation in CsCl as described in Sambrook et al (1989).

The cDNA insert from λBrhTX-1(b) 1 was removed by digestion with Not I and ligated into pBluescript SK- that had been digested with Not I and phosphatase treated. The insert of the clone was sequenced using the ABI dye-primer sequencing kit (as described above). The sequence of the plasmid clone, pBrhTX-1(b) 1, insert is given in Sequence ID No. 41 and FIG. 1. The amino acids 2744 match those of the N-terminal sequence shown in Sequence ID No. 2, but the very short apparent size of the ORF encoded by the sequence in Sequence ID No. 41 suggested that the clone was severely truncated. We therefore designed two primers to the ORF at the 5' end of the clone, namely BH(b)C and BH(b)D as shown in Sequence ID Nos. 42 and 43 respectively. Using these primers and pBrhTX-1(b)1.1 as a target we generated a $^{32}$P-labelled probe by PCR under the following conditions:

5 minutes at 95° C.;

30 seconds at 95° C.; 1.5 minutes at 45° C.; 1 minute at 72° C. (5 cycles); then 30 seconds at 95° C.; 1.5 minutes at 50° C.; 1 minute at 72° C. (5 cycles); then 5 minutes at 72° C.

The library was then re-screened using the conditions described above. Six strongly hybridising plaques were purified through to homogeneity in three rounds of plaque purification. cDNA inserts were removed from the phage by digestion with Not I and ligated into pBluescript SK- that had been digested with Not I and phosphatase treated. The sizes of the inserts were estimated by digestion with Not I and separation of restriction fragments through 0.8% agarose gels in TAE buffer.

The following cDNA insert sizes were estimated:

λBrhTX-1(b)2—about 500 bp; and λBrhTX-1(b)3, λBrhTX-1(b)4, λBrhTX-1(b)5 and λBrhTX-1(b)6 all at about 1200 bp.

The plasmid designated pBrhTX-1(b)6 was sequenced using the ABI 370 A DNA analysis system and previously described dye primers. The sequencing was completed using the ABI dye-terminator system in conjunction with the BH(b)C, BH(b)D (Sequence ID Nos. 42 and 43) primers and two additional primers as shown below and in Sequence ID Nos. 44 and 45:

```
BH(b)E         GTTGTCAATACACCCTG

BH(b)F         AGAACGAGATGTTATTGTAT
```

The nucleotide sequence obtained is shown in Sequence ID No. 46. Translation of the nucleotide sequence is shown in Sequence ID No. 47, and gives a protein of either 182 or 165 amino acids depending upon the initiation codon used. The alternative proteins have hydrophobic leader sequences of either 21 or 4 amino acids respectively, giving a mature peptide of 161 amino acids. The nucleotide sequence of subunit BrhTX-1(b) and the corresponding amino acid sequence is also shown in FIG. 12, in which the putative ORF is shown in bold text. In particular the protein translation of the cDNA is given in FIG. 13 in which the mature peptide is shown underlined.

(v) Analysis of Clones

Peptide Digestion/Sequencing

The alignment of the sequences obtained against the deduced amino acid translations is shown below:

```
Peptide Sequence    MIKPGETYGDVTNK    EWVHDNAGTLLPR cDNA Sequence       MIKPGETYGDVTNK    EWVHDNA  LLPR Peptide Sequence    PHTVYDKHESLQ      DVHDNAGTLLPR cDNA Sequence       PHTVYDKHESLY      WVHDNA  LLPQ
```

It is not unusual for the terminal amino acids to be subject to mis-sequencing; however, one of the peptide sequences sequenced on two separate occasions contains a characteristic GT amino acid pair. These GT pair is missing in the ORF predicted for the sequenced clone. We therefore deduced that the clone pBrhTX-1(b)6 contained a sequencing artefact or that the cDNA from which it was generated contained an error, i.e. a six bp deletion generated during synthesis/cloning. We therefore recloned the region containing the apparent "GT" pair/deletion by PCR. Primers BH(b)E and BH(b)F were used in the PCR experiments with cDNA as the target, to generate an amplification product. cDNA was synthesised from female *B. hebetor* mRNA as previously described for the construction of the cDNA library (Example 3).

The amplification products were then cloned into the EcoRV site of pBluescript that had been T-tailed as previously described. These clones were then sequenced and all were found to contain the same sequence as pBrhTX-1(b)6 flanking the apparent GT anomaly, but had an additional six bp corresponding to the codons for G and T, i.e. GGAACT.

From these data it would appear that the GT anomaly arose during the cDNA synthesis/cloning of the original λ clone. The consensus sequence for the pBrhTX-1(b) cDNA and the putative ORF are shown in FIG. 14 and Sequence ID Nos. 48 and 49. Such sequences are also included within scope of the present invention.

Genomic Southern Blot

Southern blots of male and female *B. hebetor* genomic DNA digested with Pst I, EcoRV, Acc I and Xho I were generated as previously described. A $^{32}$P-labelled probe was generated by PCR from the 5' region of the pBrhTX-1(b)6 clone using the primers BH(b)C and BH(b)D under the following conditions:

5 minutes at 95° C.;

30 seconds at 95° C.; 1.5 minutes at 45° C.; 1 minute at 72° C. (5 cycles); then 30 seconds at 95° C.; 1.5 minutes at 50° C.; 1 minute at 72° C. (5 cycles); then b 5minutes at 72° C.

Hybridisations were carried out with the probe as previously described. Results were identical for male and female DNA. In the Pst I digest two hybridising bands were observed of 13.0 kpb and 4.1 kbp. This result is consistent with the presence of a Pst I site in the probe hybridisation region of the cDNA sequence. The EcoRV, Acc I and Xho I digests produced single hybridising bands of 3.3 kbp, 13.0 kbp and 7.0 kbp respectively.

In a second experiment, $^{32}$P-labelled probes were made from the 3' region of the pBrhTX-1(b)5 clone using the primers BH(b)E and BH(b)F under the following conditions:

5 minutes at 95° C.;

30 seconds at 95° C.; 1.5 minutes at 45° C.; 1 minute at 72° C. (5 cycles); then 30 seconds at 95° C.; 1.5 minutes at 50° C.; 1 minute at 72° C. (5 cycles); then 5 minutes at 72° C.

These probes hybridised to Southern blots prepared as previously described using male and female genomic DNA that had been digested with Bcl I, Nde I, Bgl II and Psi I. Results were identical for male and female DNA with the Bcl I and Bgl II digests single hybridising bands of 1.7 kbp and 9.1 kbp were generated. Although these results do not fully agree with the presence of both these sites within the probe hybridising region, i.e. one would normally expect to see two hybridising bands both sites are relatively close to the ends of the probe region and the fragment containing the smaller portion of the hybridising region could well evade detection with the large probes that were used in this experiment. In the Nde I and Pst I digests, single hybridising bands of 2.4 and 22.2 kbp were detected.

EXAMPLE 7

Cloning of Subunit (c) of BrhTX-1

The N-terminal sequence shown in Sequence ID No. 3 was insufficient to attempt any PCR approaches to the isolation of the gene encoding it. Peptide fragments were therefore obtained using the peptide digestion method outlined above. These peptide sequences with their presumptive coding sequence are shown in FIG. 15 (where "?" indicates uncertainty over the first amino acid, and amino acids shown in brackets are where two possible options exist), and Sequence ID Nos. 50 and 51. From these sequences the following multi-species primers, BH(c)A and BH(c)B, were synthesised as shown below and in Sequence ID Nos. 52 and 53:

```
BH(c)A       5'-TG (ATG)CC (AGT)AC (AG)TC (AGT)GC-3'

BH(c)B       5'-GT(TCAG) CA(TC) AA(TC) CC(ACT) GG(TAC) AA-3'
```

PCR against *B. hebetor* cDNA as described above for subunit BrhTX-1(b) was carried out using these primers under the following conditions:

5 minutes at 95° C. (1 cycle) then 30 seconds at 95° C.; 1 minute at 45° C.; 1 minute at 72° C. (5 cycles) then 30 seconds at 95° C.; 1 minute at 50° C.; 1 minute at 72° C. (30 cycles) then 5 minutes at 72° C. (1 cycle).

A PCR product of approximately 300 bp was generated which was cloned into T-tailed pBluescript SK-, and sequenced as described above. The sequence of this PCR product is given in Sequence ID No. 54 and FIG. 16.

(ii) Screening of Library and Isolation of Clones

Library plating was carried out as for subunit BrhTX-1 (b). $^{32}$P-labelled probes were synthesised by PCR using the primers BH(c)A and BH(c)B and the cloned PCR product carrying the sequence shown in Sequence ID No. 54 as target DNA. The PCR was carried out under the following conditions:

5 minutes at 95° C. (1 cycle) then 30 seconds at 95° C.; 1.5 minute at 45° C.; 1 minute at 72° C. (5 cycles) then 30 seconds at 95° C.; 1.5 minute at 50° C.; 1 minute at 72° C. (30 cycles) then 5 minutes at 72° C. (1 cycle).

Five plaques were purified through to homogeneity as previously described by three rounds of plaque purification.

(iii) Characterisation of Clones

The size of the cDNA inserts were estimated by PCR using the λGT 11 forward and reverse primers as previously described. The following insert sizes were estimated:

λBrhTX-1(c)1—about 690 bp

λBrhTX-1(c)2—about 1,8000 bp

λBrhTX-1(c)3—about 690 bp

λBrhTX-1(c)4—about 700 bp

λBrhTX-1(c)6—about 690 bp.

(iv) Subcloning and Sequencing of Clones

Phage DNA was purified by isopyncnic centrifugation in CsCl as described by Sambrook et al (1989). The cDNA insert from λBrhTX-1(c)5 was liberated by digestion with Not I and was cloned into the Not I site of pBluescript SK- as previously described. This plasmid clone is designated pBrhTX-1(c)5.

The insert in pBrhTX-1 (c)5 was sequenced using the ABI dye-primers as described previously and the ABI dye-terminator sequencing system in conjunction with the following primers:

```
BH(c)F1          CGCTCTGGCAAACACTCTAT

BH(c)R1          GGTGGAGCAAGCAAACTAAA
```

This primers are also shown in Sequence ID Nos. 55 and 56.

The nucleotide sequence obtained is shown in Sequence ID No. 57. The putative translation of this cDNA sequence gave an ORF of 145 amino acids and a predicted molecular weight of 18.8 kDa, which is shown in Sequence ID No. 58. The nucleotide sequence and putative amino acid sequence of the cDNA are also shown in FIG. 17.

(v) Analysis of Clones

Peptide Digestion/Sequencing

The alignment of the N-terminal protein sequence obtained directly from the BrhTX-1(c) subunit with the deduced amino acid from the cloned cDNA is shown below:

```
Peptide Sequence      MDDGE--E--MNP--D
cDNA Sequence         MDDGETCERCLNPLEL
``` the mismatches in the latter half of the direct protein sequence can be ascribed to sequencing artefacts arising from relatively low amounts of protein available, which also accounts for the missing amino acids (which gave indecipherable peaks in the sequencing).

The alignment of the tryptic peptide sequence with the deduced amino acid sequence from the cDNA are shown below:

```
Peptide Sequence        (G/H)VHNPGNFR cDNA Sequence             H VHNPGNFR
```

The disagreement/ambiguity at the end of the sequence shown above can be ascribed to artefacts in the protein sequencing.

Genomic Southern Blot

Southern blots of male and female *B. hebetor* genomic DNA digested with Bcl I, Nde I and Bgl II were generated as previously described. A $^{32}$P-labelled probe was generated by PCR from the 5' region of the pBrhTX1(c)5 clone using the primers BH(c)F1 and BH(c)R1 under the following conditions:

5 minutes at 95° C.;

30 seconds at 95° C., 1.5 minutes at 45° C., 1 minutes at 72° C. (5 cycles); then 30 seconds at 95° C., 1.5 minutes at 50° C., 1 minutes at 72° C. (5 cycles);

5 minutes at 72° C.

Hybridisations were carried out with probe as previously described. Results were identical for male and female DNA. In the Bcl I digest two hybridising bands were observed of 3.3 kbp and 1.8 kbp. This result is consistent with the presence of a Bcl I site in the probe hybridisation region of the cDNA sequence. The Nde I and Bgl II digests produced single hybridising bands of 3.1 kbp, 17.6 kbp respectively.

Key to Codes used in Sequence Listing

| Code | Group | Nucleotide(s) |
|---|---|---|
| A | A | adenine |
| C | C | cytosine |
| G | G | guanine |
| T | T | thymine (in DNA) |
| U | U | uracil (in RNA) |
| Y | C or T(U) | pyrimidine |
| R | A or G | purine |
| M | A or C | amino |
| K | G or T(U) | keto |
| S | G or C | strong interaction (3 hydrogen bonds) |
| W | A or T(U) | weak interaction (2 hydrogen bonds) |
| H | A or C or T(U) | not-G |
| B | G or T(U) or C | not-A |
| V | G or C or A | not-T or not-U |
| D | G or A or T(U) | not-C |
| N | G,A,C or T(U) | any |

| One-Letter Code | Three-Letter Code | Amino Acid |
|---|---|---|
| A | Ala | Alanine |
| R | Arg | Arginine |
| N | Asn | Asparagine |
| D | Asp | Aspartic acid |
| C | Cys | Cysteine |
| Q | Gln | Glutamine |
| E | Glu | Glutamic acid |
| G | Gly | Glycine |
| H | His | Histidine |
| I | Ile | Isoleucine |
| L | Leu | Leucine |
| K | Lys | Lysine |
| M | Met | Methionine |
| F | Phe | Phenylalanine |
| P | Pro | Proline |
| S | Ser | Serine |
| T | Thr | Threonine |
| W | Trp | Tryptophan |
| Y | Tyr | Tyrosine |
| V | Val | Valine |
| B | Asx | Aspartic acid or Asparagine |
| Z | Glx | Glutamic acid or Glutamine |
| X | Xaa | Any amino acid |

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
       (A) LENGTH: 20 amino acids
       (B) TYPE: amino acid
       (D) TOPOLOGY: linear (ii) MOLECULE TYPE: peptide (xi) SEQUENCE DESCRIPTION: SEQ ID NO: 1:

Phe Asn Pro Glu Thr His Arg Glu Cys Lys Asn Tyr Cys Ala Lys Glu
1               5                   10                  15

His Gly Glu Glu
         20

(2) INFORMATION FOR SEQ ID NO: 2:

(i) SEQUENCE CHARACTERISTICS:
       (A) LENGTH: 18 amino acids
       (B) TYPE: amino acid
       (D) TOPOLOGY: linear (ii) MOLECULE TYPE: peptide (xi) SEQUENCE DESCRIPTION: SEQ ID NO: 2:

Thr Leu Phe Thr Asp Arg Lys Trp Ser Gly Arg Ala Asp Lys Thr Phe
1               5                   10                  15

Gly Pro (2) INFORMATION FOR SEQ ID NO: 3:

(i) SEQUENCE CHARACTERISTICS:
       (A) LENGTH: 16 amino acids
       (B) TYPE: amino acid
       (D) TOPOLOGY: linear (ii) MOLECULE TYPE: peptide (xi) SEQUENCE DESCRIPTION: SEQ ID NO: 3:

Met Asp Asp Gly Glu Xaa Xaa Glu Xaa Xaa Met Asn Pro Xaa Xaa Asp
1               5                   10                  15

(2) INFORMATION FOR SEQ ID NO: 4:

(i) SEQUENCE CHARACTERISTICS:
       (A) LENGTH: 25 amino acids
       (B) TYPE: amino acid
       (D) TOPOLOGY: linear (ii) MOLECULE TYPE: peptide (xi) SEQUENCE DESCRIPTION: SEQ ID NO: 4:

Ile Ile Asn Gly His Asp Ala Thr Glu Glu Gln Phe Pro Pro Thr Ala
1               5                   10                  15

Tyr Met Thr Arg Met Ala Arg Asn Val
         20                  25

(2) INFORMATION FOR SEQ ID NO: 5:

(i) SEQUENCE CHARACTERISTICS:

(A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 5:

TTYAAYCCNG ARACNCAYNG NGA                                              23

(2) INFORMATION FOR SEQ ID NO: 6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 6:

GCNAAAGARC ASGGNGARGA                                                  20

(2) INFORMATION FOR SEQ ID NO: 7:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 7:

TTCAACCCNG ARACNCACNG NGARNNNAAR AACTACNNNG CNAARGARCA TGGNGARGA       59

(2) INFORMATION FOR SEQ ID NO: 8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 8:

GACTCCTGGA GCCCG                                                       15

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 9:

TTGACACCAG ACCAACTGGT AATG                                             24

(2) INFORMATION FOR SEQ ID NO: 10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 10:

GCTGATGTGC TGCAAGGCGA TTAAG                                                    25

(2) INFORMATION FOR SEQ ID NO: 11:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 11:

TTCACAGAGG AAACAGCTAT GAC                                                      23

(2) INFORMATION FOR SEQ ID NO: 12:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 12:

TCGTCAAGTG AAGAATTA                                                            18

(2) INFORMATION FOR SEQ ID NO: 13:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 13:

AATGTGTTTG CACTCACG                                                            18

(2) INFORMATION FOR SEQ ID NO: 14:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 14:

CATATACAGC GAAGTACC                                                            18

(2) INFORMATION FOR SEQ ID NO: 15:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 15:

-continued

TTATATGAAG TTCTTAGA                                                18

(2) INFORMATION FOR SEQ ID NO: 16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 16:

GGCGCAATAA TTCTTCAC                                                18

(2) INFORMATION FOR SEQ ID NO: 17:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 17:

TAACTATGGG ATTCTTAG                                                18

(2) INFORMATION FOR SEQ ID NO: 18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 18:

ATATTTAAAG CCTCCCGC                                                18

(2) INFORMATION FOR SEQ ID NO: 19:

(i) SEQUENCE CHARACTERISTICS:
        (A) LENGTH: 563 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 13..387

(xi) SEQUENCE DESCRIPTION: SEQ ID NO: 19:

TTTGGATAAA TC ATG AAA TTT TTA TAT CTA ATA CTC CTT TTA ATT GCA       48
              Met Lys Phe Leu Tyr Leu Ile Leu Leu Leu Ile Ala
                1               5                  10

GGA GTA GTA TCA TTC AAT CCG GAG ACA CAT CGT GAA TGT AAG AAT TAT    96
Gly Val Val Ser Phe Asn Pro Glu Thr His Arg Glu Cys Lys Asn Tyr
            15                  20                  25

TGC GCC AAA GAG CAC GGC GAG GAA TAT CGT ACG TGG TCT TTC CGT TAC   144
Cys Ala Lys Glu His Gly Glu Glu Tyr Arg Thr Trp Ser Phe Arg Tyr
        30                  35                  40

GAA CTT GGT GAT ATT TTT AAA TGT GTT TGC ACT CAC GGA AAG AAT CTT   192
Glu Leu Gly Asp Ile Phe Lys Cys Val Cys Thr His Gly Lys Asn Leu

```
                45                  50                  55                  60
ATG GGA AGC GAG AAT TAT GGT AAG TGT AGA GAA GCA TGT ATT CAA AAT            240
Met Gly Ser Glu Asn Tyr Gly Lys Cys Arg Glu Ala Cys Ile Gln Asn
                        65                  70                  75

CAT GGA GCG GGA GGC TTT AAA TAT GCC TTT CCC ATA TAC AGC GAA GTA            288
His Gly Ala Gly Gly Phe Lys Tyr Ala Phe Pro Ile Tyr Ser Glu Val
            80                  85                  90

CCA GCA TCA TGG GCA TGC ATA TCA CTC AGG AGA AAA ATA AGA CAT TTT            336
Pro Ala Ser Trp Ala Cys Ile Ser Leu Arg Arg Lys Ile Arg His Phe
        95                  100                 105

GTA TAC ATG CTT GCT CAG AAA TTC ATC ACA AGG CCC CAC CTA AGA ATC            384
Val Tyr Met Leu Ala Gln Lys Phe Ile Thr Arg Pro His Leu Arg Ile
    110                 115                 120

CCA TAGTTATGAA AAATGGACAA TGCTACTACC AAGATCACAG GGGTGTTGAC                  437
Pro
125

AGGTATTGTG AAGTTTATAT GAAGTTCTTA GATGCGTTGG AATCAATTTA ACAATGATCA           497

AATTCATGTT ATCAATGAAG GAAGAATAAT GAATTAATAA TAATTATCAA AAATCAAAAA           557

AAAAAA                                                                      563

(2) INFORMATION FOR SEQ ID NO: 20:

(i) SEQUENCE CHARACTERISTICS:
        (A) LENGTH: 125 amino acids
        (B) TYPE: amino acid
        (D) TOPOLOGY: linear (ii) MOLECULE TYPE: protein (xi) SEQUENCE DESCRIPTION: SEQ ID NO: 20:

Met Lys Phe Leu Tyr Leu Ile Leu Leu Ile Ala Gly Val Val Ser
 1               5                  10                  15

Phe Asn Pro Glu Thr His Arg Glu Cys Lys Asn Tyr Cys Ala Lys Glu
                20                  25                  30

His Gly Glu Glu Tyr Arg Thr Trp Ser Phe Arg Tyr Glu Leu Gly Asp
        35                  40                  45

Ile Phe Lys Cys Val Cys Thr His Gly Lys Asn Leu Met Gly Ser Glu
    50                  55                  60

Asn Tyr Gly Lys Cys Arg Glu Ala Cys Ile Gln Asn His Gly Ala Gly
65                  70                  75                  80

Gly Phe Lys Tyr Ala Phe Pro Ile Tyr Ser Glu Val Pro Ala Ser Trp
                85                  90                  95

Ala Cys Ile Ser Leu Arg Arg Lys Ile Arg His Phe Val Tyr Met Leu
            100                 105                 110

Ala Gln Lys Phe Ile Thr Arg Pro His Leu Arg Ile Pro
        115                 120                 125

(2) INFORMATION FOR SEQ ID NO: 21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 21:

ATNATNAAYG GNCAYGAYGC NAC                                                   23
```

(2) INFORMATION FOR SEQ ID NO: 22:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 22:

GAYGCNACNG ARGARCARTT YCC                                          23

(2) INFORMATION FOR SEQ ID NO: 23:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 23:

ATNATNAWCG GNCATGWCGC NACNGARCAR TTYCCNCCNA CNGANTAYAT GACNNGNATG      60

GCNNGNAAYG T                                                              71

(2) INFORMATION FOR SEQ ID NO: 24:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 24:

CTTCAAATTA GTGTACGA                                                  18

(2) INFORMATION FOR SEQ ID NO: 25:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 25:

TGTGGCAATG CACAGAAC                                                  18

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 26:

TCAAGATGCT AGATTGTC                                                  18

(2) INFORMATION FOR SEQ ID NO: 27:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (ii) MOLECULE TYPE: DNA (xi) SEQUENCE DESCRIPTION: SEQ ID NO: 27:

TAATAAATGG TCATGATG                                                    18

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 28:

CGCTTTCAAA TAGTCACT                                                    18

(2) INFORMATION FOR SEQ ID NO: 29:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 29:

ATTCACCATC TGAGCAAT                                                    18

(2) INFORMATION FOR SEQ ID NO: 30:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 30:

ACACAATTAG CCACTGTC                                                    18

(2) INFORMATION FOR SEQ ID NO: 31:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 31:

TTGTACTCAG AATGGACT                                                    18

(2) INFORMATION FOR SEQ ID NO: 32:

(i) SEQUENCE CHARACTERISTICS:
        (A) LENGTH: 18 base pairs
        (B) TYPE: nucleic acid (C) STRANDEDNESS: single
            (D) TOPOLOGY: linear (ii) MOLECULE TYPE: DNA (xi) SEQUENCE DESCRIPTION: SEQ ID NO: 32:

ATGTATGGAG CGATACCA                                                   18

(2) INFORMATION FOR SEQ ID NO: 33:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 33:

ACATCATGAA TTGCCTTG                                                   18

(2) INFORMATION FOR SEQ ID NO: 34:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 34:

TGTAAATGTG TAGTGGGT                                                   18

(2) INFORMATION FOR SEQ ID NO: 35:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 35:

GCGAGAAATT CACTATCA                                                   18

(2) INFORMATION FOR SEQ ID NO: 36:

(i) SEQUENCE CHARACTERISTICS:
            (A) LENGTH: 1058 base pairs
            (B) TYPE: nucleic acid
            (C) STRANDEDNESS: single
            (D) TOPOLOGY: linear (ii) MOLECULE TYPE: cDNA (ix) FEATURE:
            (A) NAME/KEY: CDS
            (B) LOCATION: 95..919

(xi) SEQUENCE DESCRIPTION: SEQ ID NO: 36:

CGCGGCCGCT GTTGATATAT AACAATTTAT TAAAAATTTC AAGTGGAAAG AAAAACTATC     60

TTGTTTTTTT TTTTGTTTTT TTTCATAATT TAAA ATG CAT TTC TTC GCC TCC        112
                                     Met His Phe Phe Ala Ser
                                       1               5

ATC CTG GTA TCC TTC TTA CTG GGC AAG GCA ATT CAT GAT GTG GAA GGA      160
Ile Leu Val Ser Phe Leu Leu Gly Lys Ala Ile His Asp Val Glu Gly

```
                10                   15                   20
ATA ATA AAT GGT CAT GAT GCT ACT GAG GGA CAA TTT CCC CAT ATG GCT        208
Ile Ile Asn Gly His Asp Ala Thr Glu Gly Gln Phe Pro His Met Ala
            25                  30                  35

TAT TTA CAA GCA TCA GCT GGA AAG TGT TCT TAT GTA TGT GGC GGT GCT        256
Tyr Leu Gln Ala Ser Ala Gly Lys Cys Ser Tyr Val Cys Gly Gly Ala
        40                  45                  50

CTT CTA ACT AAA AAA CAT ATT ATG ACA GCT GCT CAT TGT GTA GCA ATG        304
Leu Leu Thr Lys Lys His Ile Met Thr Ala Ala His Cys Val Ala Met
55                  60                  65                  70

CAC AGA ACG GGA AAT ATT AAA GTA GCC CTT GGT GTT ACG GAT TTT CAT        352
His Arg Thr Gly Asn Ile Lys Val Ala Leu Gly Val Thr Asp Phe His
                75                  80                  85

AAT AAG CCA TCA ATG CAA CAA AGA AAG GTT GAA CAT ATA AAA GTC CAT        400
Asn Lys Pro Ser Met Gln Gln Arg Lys Val Glu His Ile Lys Val His
            90                  95                  100

TCT GAG TAC AAA GGA GGA AGG CGT AAG TCA TTA AAA AAT TGG TAT CGC        448
Ser Glu Tyr Lys Gly Gly Arg Arg Lys Ser Leu Lys Asn Trp Tyr Arg
        105                 110                 115

TCC ATA CAT CGT ACA TTT ACA GGA CCG TCT GGG GAT AAA GAA TAC AAT        496
Ser Ile His Arg Thr Phe Thr Gly Pro Ser Gly Asp Lys Glu Tyr Asn
    120                 125                 130

GAT ATT GCT ATT ATA ACG TTG AGC CAG GAA GTA ACA CTA GGA CCA GTA        544
Asp Ile Ala Ile Ile Thr Leu Ser Gln Glu Val Thr Leu Gly Pro Val
135                 140                 145                 150

GTA AAG ACT ATT AAT TTA CCC CCA AAG AGC TAT CGG CTT CCT TTT GAT        592
Val Lys Thr Ile Asn Leu Pro Pro Lys Ser Tyr Arg Leu Pro Phe Asp
                155                 160                 165

CAA GAT GCT AGA TTG TCG GGC TTT GGG CGA ACA GTC ATT GTC AAA GAA        640
Gln Asp Ala Arg Leu Ser Gly Phe Gly Arg Thr Val Ile Val Lys Glu
            170                 175                 180

AAT GAT CCA ATT CCT CCA CCC ACT ACA CAT TTA CAA TGG CTA GAT ATG        688
Asn Asp Pro Ile Pro Pro Pro Thr Thr His Leu Gln Trp Leu Asp Met
        185                 190                 195

AAG GTT CTT CAT TCA CGA GAT GCT ATT GTC ACT GAT AGT GAA TTT CTC        736
Lys Val Leu His Ser Arg Asp Ala Ile Val Thr Asp Ser Glu Phe Leu
    200                 205                 210

GCT GAT AAA GAA TAT GGT GAT GGA ACT TGG TCT AAT GCA GCT AAG GGA        784
Ala Asp Lys Glu Tyr Gly Asp Gly Thr Trp Ser Asn Ala Ala Lys Gly
215                 220                 225                 230

GAC AGC GGT AGT CCC TTA GTC AAG GAT AAT CAA GTA ATT GGC GTA GCC        832
Asp Ser Gly Ser Pro Leu Val Lys Asp Asn Gln Val Ile Gly Val Ala
                235                 240                 245

GTT TCT GTG AGT GAT GAA GAA CAT ACT ACA CGC TTT CAA ATA GTC ACT        880
Val Ser Val Ser Asp Glu Glu His Thr Thr Arg Phe Gln Ile Val Thr
            250                 255                 260

TAT TAT TTG GAT TGG ATC AAG AAA TAT GCC GAA CTT GCG TAAAAAGAAT         929
Tyr Tyr Leu Asp Trp Ile Lys Lys Tyr Ala Glu Leu Ala
        265                 270                 275

AAAGAGCAAA ATTGCTCAGA TGGTGAATAT ACATTTTTCC AATAAGCTCA GAAAAAATCG      989

ATTTATATGT AATTAAAAAA ATTAAAGATT GTTTTTCTC TTTTAACAGA AGAATTTGGC      1049

GCGTGAATT                                                            1058

(2) INFORMATION FOR SEQ ID NO: 37:

(i) SEQUENCE CHARACTERISTICS:
        (A) LENGTH: 275 amino acids
        (B) TYPE: amino acid
        (D) TOPOLOGY: linear
```

(ii) MOLECULE TYPE: protein (xi) SEQUENCE DESCRIPTION: SEQ ID NO: 37:

| Met | His | Phe | Phe | Ala | Ser | Ile | Leu | Val | Ser | Phe | Leu | Leu | Gly | Lys | Ala |
|---|---|---|---|---|---|---|---|---|---|---|---|---|---|---|---|
| 1 | | | | 5 | | | | | 10 | | | | | 15 | |

| Ile | His | Asp | Val | Glu | Gly | Ile | Ile | Asn | Gly | His | Asp | Ala | Thr | Glu | Gly |
|---|---|---|---|---|---|---|---|---|---|---|---|---|---|---|---|
| | | | 20 | | | | | 25 | | | | | 30 | | |

| Gln | Phe | Pro | His | Met | Ala | Tyr | Leu | Gln | Ala | Ser | Ala | Gly | Lys | Cys | Ser |
|---|---|---|---|---|---|---|---|---|---|---|---|---|---|---|---|
| | | 35 | | | | | 40 | | | | | 45 | | | |

| Tyr | Val | Cys | Gly | Gly | Ala | Leu | Leu | Thr | Lys | Lys | His | Ile | Met | Thr | Ala |
|---|---|---|---|---|---|---|---|---|---|---|---|---|---|---|---|
| | 50 | | | | | 55 | | | | | 60 | | | | |

| Ala | His | Cys | Val | Ala | Met | His | Arg | Thr | Gly | Asn | Ile | Lys | Val | Ala | Leu |
|---|---|---|---|---|---|---|---|---|---|---|---|---|---|---|---|
| 65 | | | | | 70 | | | | | 75 | | | | | 80 |

| Gly | Val | Thr | Asp | Phe | His | Asn | Lys | Pro | Ser | Met | Gln | Gln | Arg | Lys | Val |
|---|---|---|---|---|---|---|---|---|---|---|---|---|---|---|---|
| | | | | 85 | | | | | 90 | | | | | 95 | |

| Glu | His | Ile | Lys | Val | His | Ser | Glu | Tyr | Lys | Gly | Gly | Arg | Arg | Lys | Ser |
|---|---|---|---|---|---|---|---|---|---|---|---|---|---|---|---|
| | | | 100 | | | | | 105 | | | | | 110 | | |

| Leu | Lys | Asn | Trp | Tyr | Arg | Ser | Ile | His | Arg | Thr | Phe | Thr | Gly | Pro | Ser |
|---|---|---|---|---|---|---|---|---|---|---|---|---|---|---|---|
| | | 115 | | | | | 120 | | | | | 125 | | | |

| Gly | Asp | Lys | Glu | Tyr | Asn | Asp | Ile | Ala | Ile | Thr | Leu | Ser | Gln | Glu |
|---|---|---|---|---|---|---|---|---|---|---|---|---|---|---|
| 130 | | | | | 135 | | | | | 140 | | | | |

| Val | Thr | Leu | Gly | Pro | Val | Val | Lys | Thr | Ile | Asn | Leu | Pro | Pro | Lys | Ser |
|---|---|---|---|---|---|---|---|---|---|---|---|---|---|---|---|
| 145 | | | | | 150 | | | | | 155 | | | | | 160 |

| Tyr | Arg | Leu | Pro | Phe | Asp | Gln | Asp | Ala | Arg | Leu | Ser | Gly | Phe | Gly | Arg |
|---|---|---|---|---|---|---|---|---|---|---|---|---|---|---|---|
| | | | | 165 | | | | | 170 | | | | | 175 | |

| Thr | Val | Ile | Val | Lys | Glu | Asn | Asp | Pro | Ile | Pro | Pro | Thr | Thr | His |
|---|---|---|---|---|---|---|---|---|---|---|---|---|---|---|
| | | | 180 | | | | | 185 | | | | | 190 | |

| Leu | Gln | Trp | Leu | Asp | Met | Lys | Val | Leu | His | Ser | Arg | Asp | Ala | Ile | Val |
|---|---|---|---|---|---|---|---|---|---|---|---|---|---|---|---|
| | | | 195 | | | | | 200 | | | | | 205 | | |

| Thr | Asp | Ser | Glu | Phe | Leu | Ala | Asp | Lys | Glu | Tyr | Gly | Asp | Gly | Thr | Trp |
|---|---|---|---|---|---|---|---|---|---|---|---|---|---|---|---|
| 210 | | | | | 215 | | | | | 220 | | | | | |

| Ser | Asn | Ala | Ala | Lys | Gly | Asp | Ser | Gly | Ser | Pro | Leu | Val | Lys | Asp | Asn |
|---|---|---|---|---|---|---|---|---|---|---|---|---|---|---|---|
| 225 | | | | | 230 | | | | | 235 | | | | | 240 |

| Gln | Val | Ile | Gly | Val | Ala | Val | Ser | Val | Ser | Asp | Glu | Glu | His | Thr | Thr |
|---|---|---|---|---|---|---|---|---|---|---|---|---|---|---|---|
| | | | 245 | | | | | 250 | | | | | 255 | | |

| Arg | Phe | Gln | Ile | Val | Thr | Tyr | Tyr | Leu | Asp | Trp | Ile | Lys | Lys | Tyr | Ala |
|---|---|---|---|---|---|---|---|---|---|---|---|---|---|---|---|
| | | | 260 | | | | | 265 | | | | | 270 | | |

| Glu | Leu | Ala |
|---|---|---|
| | | 275 |

(2) INFORMATION FOR SEQ ID NO: 38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 38:

ACHTTGTTYA CHGAYCGYAA                                      20

(2) INFORMATION FOR SEQ ID NO: 39:

(i) SEQUENCE CHARACTERISTICS:
        (A) LENGTH: 17 base pairs (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 39:

```
GGDCCRAADG TYTTRTC                                                    17
```

(2) INFORMATION FOR SEQ ID NO: 40:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 40:

```
ACCTTGTTTA CAGACCGCAA GTGGTGTGGA CGTGCCGATA AGACTTTCGG CCC            53
```

(2) INFORMATION FOR SEQ ID NO: 41:

(i) SEQUENCE CHARACTERISTICS:
        (A) LENGTH: 462 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 41:

```
AATTTTTCCT CATAACAATG TCAATCATAT GTAAAATAAT CTTGTTGGTG CTACTGAGTT     60

GGACATCGAT GGTATCGTCA ACATTATTTA CAGACCGAAA GTGGTGTGGA CGTGCCGATA    120

AGACTTTTGG TCCTTCACGG TCGCTAGGAG GAGGTGTTGG TGATTGCTGC AGAAGTCATA    180

ACAGCTGTGG CCGCATGATT AAACCAGGAG AGACTTATGG AGATGTTACG AATAAAGGAT    240

TTTCAAATAT GTAATGTCTG ATGATTATTA CCAACACTAA ATCTTGATTA AGAAGCTGTA    300

AAAATATCAT TTTGAGGAAA TACTCGATAT TTTTACTTTC CTCCGAATGT TATTTCTTCA    360

GCTTTTCAAC TAAAATTTCT TAATCAACTT GACAATTGTT AAAAATAACA TATTTAATTA    420

TGATTATTAT TTATTTGATT AAAGTTGGGA AAAAAAAAAC TG                       462
```

(2) INFORMATION FOR SEQ ID NO: 42:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 42:

```
ACATTATTTA CAGACCGAA                                                  19
```

(2) INFORMATION FOR SEQ ID NO: 43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 43:

CTGAATACCT CTACAATGCT 20

(2) INFORMATION FOR SEQ ID NO: 44:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 44:

GTTGTCAATA CACCCTG 17

(2) INFORMATION FOR SEQ ID NO: 45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 45:

AGAACGAGAT GTTATTGTAT 20

(2) INFORMATION FOR SEQ ID NO: 46:

(i) SEQUENCE CHARACTERISTICS:
        (A) LENGTH: 1197 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 46:

```
CACGCCTACT TAGATAATTT CTCAATTCTT TGCAAATTAT GAAATAAGTG CAAGAGATGT      60
GTATGACACC TCAATCTGAG TTTGTTCATA ATTCGAGAGG GATAAATAAG GAAGTCTCTG     120
TGTACAAAAG AAAACTACCT CATATAAATC TTGCATTTTT CCGTGAGAGA GAAAAAAAAA     180
CCCTGAAAAA CTGAGTAAGG CAATAATTTT NCCTCATAAC AATGTCAATC ATATGTAAAA     240
TAATCTTGTT GGTGCTACTG AGTTGGACAT CGATGGTATC GTCAACATTA TTTACAGACC     300
GAAAGTGGTG TGGACGTGCC GATAAGACTT TTGGTCCTTC ACGGTCGCTA GGAGGAGGTG     360
TTGGTGATTG CTGCAGAAGT CATGACAGCT GTGGCCGCAT GATTAAACCA GGAGAGACTT     420
ATGGAGATGT TACGAATAAA GGATTTTCAA ATATTTGGGA ATGCCGATGT GACTATGCAT     480
TTTTTCAATG TCTTCAGCGT TCCAATGGTA AAATGAAAAA TGTTGTGGAA ATATTGCATT     540
TTGACGTTGT CAATACACCC TGTTACTTCA TGAAAGATGG CCGTGCTAAA ATATCACCCC     600
ATACTGTATA TGATAAACAC GAATCACTCT ATCAACTTAT ACTACACAAA GATAATTTTA     660
AGGAGTGGGT GCATGATAAT GCTCTTCTCC CGCAAGAGCT GGGGATTAAA GATGAGCATG     720
TGTGGGAGAC ACTGATGGCA TGGATGGACT TTAGATTTCC AACTGAATAA TAAATATTCC     780
AAATACAGAT ATCCTTTTGA TAAAATGTCG TAAACATGAT TGTTTAGATG AATGGTAAAT     840
TAATGAAAAG ATTGATTGAA AATGTCTGAA GTAACTNNNG GATNNGACAT ATAATATATA     900
ATATTTGCCT TATTNGATAA ACTTCTACCN TTAANAAAGG AAAAAGGAGG AGGNGTAGGA     960
```

```
GGAGGATTAG GATATTTTAC AAGGATTTTA AAAATAATTA AACAATTAGA TCTTCTGTAA      1020

ATTGATTGAT CATGTATTAA ATACAATAAC ATCTCGTTCT CATAGTACAA TGAAAAAGAA      1080

CATAACAGTA TGCACAAAAA TAATGACGGT AAATATCTAT GTATGTATGT AGAGAGAAGA      1140

AAATAAAAAT AGTTAGACAG GTACCAAAAA AAAAAAAAAA AAAAAAAAAA AAAAAAA         1197
```

(2) INFORMATION FOR SEQ ID NO: 47:

(i) SEQUENCE CHARACTERISTICS:
        (A) LENGTH: 182 amino acids
        (B) TYPE: amino acid
        (D) TOPOLOGY: linear (ii) MOLECULE TYPE: protein (xi) SEQUENCE DESCRIPTION: SEQ ID NO: 47:

```
Met Ser Ile Ile Cys Lys Ile Ile Leu Leu Val Leu Leu Ser Trp Thr
1               5                   10                  15

Ser Met Val Ser Ser Thr Leu Phe Thr Asp Arg Lys Trp Cys Gly Arg
                20                  25                  30

Ala Asp Lys Thr Phe Gly Pro Ser Arg Ser Leu Gly Gly Val Gly
            35                  40                  45

Asp Cys Cys Arg Ser His Asp Ser Cys Gly Arg Met Ile Lys Pro Gly
        50                  55                  60

Glu Thr Tyr Gly Asp Val Thr Asn Lys Gly Phe Ser Asn Ile Trp Glu
65                  70                  75                  80

Cys Arg Cys Asp Tyr Ala Phe Phe Gln Cys Leu Gln Arg Ser Asn Gly
                85                  90                  95

Lys Met Lys Asn Val Val Glu Ile Leu His Phe Asp Val Val Asn Thr
                100                 105                 110

Pro Cys Tyr Phe Met Lys Asp Gly Arg Ala Lys Ile Ser Pro His Thr
            115                 120                 125

Val Tyr Asp Lys His Glu Ser Leu Tyr Gln Leu Ile Leu His Lys Asp
        130                 135                 140

Asn Phe Lys Glu Trp Val His Asp Asn Ala Leu Leu Pro Gln Glu Leu
145                 150                 155                 160

Gly Ile Lys Asp Glu His Val Trp Glu Thr Leu Met Ala Trp Met Asp
                165                 170                 175

Phe Arg Phe Pro Thr Glu
            180
```

(2) INFORMATION FOR SEQ ID NO: 48:

(i) SEQUENCE CHARACTERISTICS:
        (A) LENGTH: 1201 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 222..773

(xi) SEQUENCE DESCRIPTION: SEQ ID NO: 48:

```
CACGCCTACT TAGATAATTT CTCAATTCTT TGCAAATTAT GAAATAAGTG CAAGAGATGT        60

GTATGACACC TCAATCTGAG TTTGTTCATA ATTCGAGAGG GATAAATAAG GAAGTCTCTG       120

TGTACAAAAG AAAACTACCT CATATAAATC TTGCATTTTT CCGTGAGAGA GAAAAAAAAA       180
```

```
CCCTGAAAAA CTGAGTAAGG CAATAATTTT CCCTCATAAC A ATG TCA ATC ATA      233
                                              Met Ser Ile Ile
                                                1

TGT AAA ATA ATC TTG TTG GTG CTA CTG AGT TGG ACA TCG ATG GTA TCG    281
Cys Lys Ile Ile Leu Leu Val Leu Leu Ser Trp Thr Ser Met Val Ser
 5              10                  15                  20

TCA ACA TTA TTT ACA GAC CGA AAG TGG TGT GGA CGT GCC GAT AAG ACT    329
Ser Thr Leu Phe Thr Asp Arg Lys Trp Cys Gly Arg Ala Asp Lys Thr
                25                  30                  35

TTT GGT CCT TCA CGG TCG CTA GGA GGA GGT GTT GGT GAT TGC TGC AGA    377
Phe Gly Pro Ser Arg Ser Leu Gly Gly Gly Val Gly Asp Cys Cys Arg
            40                  45                  50

AGT CAT GAC AGC TGT GGC CGC ATG ATT AAA CCA GGA GAG ACT TAT GGA    425
Ser His Asp Ser Cys Gly Arg Met Ile Lys Pro Gly Glu Thr Tyr Gly
        55                  60                  65

GAT GTT ACG AAT AAA GGA TTT TCA AAT ATT TGG GAA TGC CGA TGT GAC    473
Asp Val Thr Asn Lys Gly Phe Ser Asn Ile Trp Glu Cys Arg Cys Asp
    70                  75                  80

TAT GCA TTT TTT CAA TGT CTT CAG CGT TCC AAT GGT AAA ATG AAA AAT    521
Tyr Ala Phe Phe Gln Cys Leu Gln Arg Ser Asn Gly Lys Met Lys Asn
 85                  90                  95                 100

GTT GTG GAA ATA TTG CAT TTT GAC GTT GTC AAT ACA CCC TGT TAC TTC    569
Val Val Glu Ile Leu His Phe Asp Val Val Asn Thr Pro Cys Tyr Phe
                105                 110                 115

ATG AAA GAT GGC CGT GCT AAA ATA TCA CCC CAT ACT GTA TAT GAT AAA    617
Met Lys Asp Gly Arg Ala Lys Ile Ser Pro His Thr Val Tyr Asp Lys
            120                 125                 130

CAC GAA TCA CTC TAT CAA CTT ATA CTA CAC AAA GAT AAT TTT AAG GAG    665
His Glu Ser Leu Tyr Gln Leu Ile Leu His Lys Asp Asn Phe Lys Glu
        135                 140                 145

TGG GTG CAT GAT AAT GCT GGA ACT CTT CTC CCG CAA GAG CTG GGG ATT    713
Trp Val His Asp Asn Ala Gly Thr Leu Leu Pro Gln Glu Leu Gly Ile
    150                 155                 160

AAA GAT GAG CAT GTG TGG GAG ACA CTG ATG GCA TGG ATG GAC TTT AGA    761
Lys Asp Glu His Val Trp Glu Thr Leu Met Ala Trp Met Asp Phe Arg
165                 170                 175                 180

TTT CCA ACT GAA TAATAAATAT TCCAAATACA GATATCCTTT TGATAAAATG        813
Phe Pro Thr Glu

TCGTAAACAT GATTGTTTAG ATGAATGGTA AATTAATGAA AAGATTGATT GAAAATGTCT  873

GAAGTAACTT TTGGATTTTA CATATAATAT ATAATATTTG CCTTATTGA TAAACTTCTA   933

AATTAAAAAA GAAAAAGGAG GAGGAGTAGG AGGAGGATTA GGATATTTTA CAAGGATTTT  993

AAAAATAATT AAACAATTAG ATCTTCTGTA AATTGATTGA TCATGTATTA AATACAATAA  1053

CATCTCGTTC TCATAGTACA ATGAAAAAGA ACATAACAGT ATGCACAAAA ATAATGACGG  1113

TAAATATCTA TGTATGTATG TAGAGAGAAG AAAATAAAAA TAGTTAGACA GGTACCAAAA  1173

AAAAAAAAAA AAAAAAAAA AAAAAAA                                      1201
```

(2) INFORMATION FOR SEQ ID NO: 49:

(i) SEQUENCE CHARACTERISTICS:
        (A) LENGTH: 184 amino acids
        (B) TYPE: amino acid
        (D) TOPOLOGY: linear (ii) MOLECULE TYPE: protein (xi) SEQUENCE DESCRIPTION: SEQ ID NO: 49:

Met Ser Ile Ile Cys Lys Ile Ile Leu Leu Val Leu Leu Ser Trp Thr

```
            1               5                    10                   15
        Ser Met Val Ser Ser Thr Leu Phe Thr Asp Arg Lys Trp Cys Gly Arg
                        20                  25                  30

Ala Asp Lys Thr Phe Gly Pro Ser Arg Ser Leu Gly Gly Gly Val Gly
                    35                  40                  45

Asp Cys Cys Arg Ser His Asp Ser Cys Gly Arg Met Ile Lys Pro Gly
                50                  55                  60

Glu Thr Tyr Gly Asp Val Thr Asn Lys Gly Phe Ser Asn Ile Trp Glu
        65                  70                  75                  80

Cys Arg Cys Asp Tyr Ala Phe Phe Gln Cys Leu Gln Arg Ser Asn Gly
                        85                  90                  95

Lys Met Lys Asn Val Val Glu Ile Leu His Phe Asp Val Val Asn Thr
                        100                 105                 110

Pro Cys Tyr Phe Met Lys Asp Gly Arg Ala Lys Ile Ser Pro His Thr
                        115                 120                 125

Val Tyr Asp Lys His Glu Ser Leu Tyr Gln Leu Ile Leu His Lys Asp
        130                 135                 140

Asn Phe Lys Glu Trp Val His Asp Asn Ala Gly Thr Leu Leu Pro Gln
        145                 150                 155                 160

Glu Leu Gly Ile Lys Asp Glu His Val Trp Glu Thr Leu Met Ala Trp
                        165                 170                 175

Met Asp Phe Arg Phe Pro Thr Glu
                        180

(2) INFORMATION FOR SEQ ID NO: 50:

(i) SEQUENCE CHARACTERISTICS:
            (A) LENGTH: 24 amino acids
            (B) TYPE: amino acid
            (D) TOPOLOGY: linear (ii) MOLECULE TYPE: peptide (xi) SEQUENCE DESCRIPTION: SEQ ID NO: 50:

Xaa Ile Ala Xaa Asp Val Gly His Ala Ala His Ser Phe Thr Lys Xaa
    1               5                   10                  15

Val His Asn Pro Gly Asn Phe Arg
                    20

(2) INFORMATION FOR SEQ ID NO: 51:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO: 51:

ATHGCNCARG AYGTNGGDCA YGCNGCNCAY WSNTTYACNA ARGTNCAYAA YCCNGGNAAY      60

TTYMGN                                                                66

(2) INFORMATION FOR SEQ ID NO: 52:

(i) SEQUENCE CHARACTERISTICS:
            (A) LENGTH: 14 base pairs
            (B) TYPE: nucleic acid
            (C) STRANDEDNESS: single
            (D) TOPOLOGY: linear
```

(ii) MOLECULE TYPE: DNA (xi) SEQUENCE DESCRIPTION: SEQ ID NO: 52:

TGDCCDACRT CDGC 14

(2) INFORMATION FOR SEQ ID NO: 53:

(i) SEQUENCE CHARACTERISTICS:
       (A) LENGTH: 17 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 53:

GTNCAYAAYC CHGGHAA 17

(2) INFORMATION FOR SEQ ID NO: 54:

(i) SEQUENCE CHARACTERISTICS:
       (A) LENGTH: 275 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 54:

GTGCACAATC CAGGAAACTT CCGAGTCTCC AAATGTGTAT GCGACATTGC GCTCAAGGAG 60

TGCCTCACTA CTCATCCTGA AATGAGTTTC AAATTTGTTA AAGCACTCTT TTTTGATTTG 120

CTTGCTCCAC CCTGTTTTGA TCAGATTGCT GATTGGGGTA AGAAAAAATT GAAAAATAAG 180

CAGGCATTTT CACTGCATGA TTTACAATCA GCTGCCCACG CGCTCTGGCA AACACTCTAT 240

GACGCTGTCA AGGGCATAGC TCAAGATGTC GGCCA 275

(2) INFORMATION FOR SEQ ID NO: 55:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 55:

CGCTCTGGCA AACACTCTAT 20

(2) INFORMATION FOR SEQ ID NO: 56:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: DNA (xi) SEQUENCE DESCRIPTION: SEQ ID NO: 56:

GGTGGAGCAA GCAAACTAAA 20

(2) INFORMATION FOR SEQ ID NO: 57:

(i) SEQUENCE CHARACTERISTICS:
       (A) LENGTH: 685 base pairs (B) TYPE: nucleic acid
          (C) STRANDEDNESS: single
          (D) TOPOLOGY: linear (ii) MOLECULE TYPE: cDNA (ix) FEATURE:
          (A) NAME/KEY: CDS
          (B) LOCATION: 156..590

(xi) SEQUENCE DESCRIPTION: SEQ ID NO: 57:

GCGCGCGCAG CAAGACTAAG AGTAAGAGAG GGGAACATAG AAGAGTGTTT ACAATAGTGG        60

AGATGTGGGG GCTTTCATTT CTATTAGTTC CGTGCTGGAG TTTTTCAACC TACGCTGGGT       120

GTGGTGGATA TAATCGGTCC ATTACTAAGC GACAG ATG GAC GAT GGT GAG ACG         173
                                      Met Asp Asp Gly Glu Thr
                                        1               5

TGC GAA AGG TGT TTG AAT CCA CTC GAA TTA GTA AAT GAC GCT GTA GAC         221
Cys Glu Arg Cys Leu Asn Pro Leu Glu Leu Val Asn Asp Ala Val Asp
             10                  15                  20

TCG TGC ATT GAA GCT CAT GAG GAA TGT GAG GAA TTC ATG GAA GGC GGG         269
Ser Cys Ile Glu Ala His Glu Glu Cys Glu Glu Phe Met Glu Gly Gly
         25                  30                  35

ATG GAA ATG CTT CAT GTA CAC AAT CCA GGA AAC TTC CGA GTC TCC AAA         317
Met Glu Met Leu His Val His Asn Pro Gly Asn Phe Arg Val Ser Lys
 40                  45                  50

TGT GTA TGC GAC ATT GCG CTC AAG GAG TGC CTC ACT ACT CAT CCT GAA         365
Cys Val Cys Asp Ile Ala Leu Lys Glu Cys Leu Thr Thr His Pro Glu
55                  60                  65                  70

ATG AGT TTC AAA TCT GTT AAA GCA CTC TTT TTT GAT TTG CTT GCT CCA         413
Met Ser Phe Lys Ser Val Lys Ala Leu Phe Phe Asp Leu Leu Ala Pro
                 75                  80                  85

CCC TGT TTT GAC CAG ATT GCT GAT TGG GGT AAG AAA AAA TTG AAA AAT         461
Pro Cys Phe Asp Gln Ile Ala Asp Trp Gly Lys Lys Lys Leu Lys Asn
             90                  95                 100

AAG CAG GCA TTT CCA CTG CAT GAT TTA CAA TCA GCT GCC CAC GCG CTC         509
Lys Gln Ala Phe Pro Leu His Asp Leu Gln Ser Ala Ala His Ala Leu
        105                 110                 115

TGG CAA ACA CTC TAT GAC GCT GTC AAG GGC ATA GCT CAG GAT GTC GGA         557
Trp Gln Thr Leu Tyr Asp Ala Val Lys Gly Ile Ala Gln Asp Val Gly
    120                 125                 130

CAT GCT GCA CAT TCT TTT GAA AAA ATG TTA CAG TAACAGTTAA ATATGAAAAA       610
His Ala Ala His Ser Phe Glu Lys Met Leu Gln
135                 140                 145

GGTCCATGAT AGTAGAATAC AGTTATTGTT GTATAAATAA ATAATATATT CAGAATGATA       670

AAAAAAAACG GCCGC                                                        685

(2) INFORMATION FOR SEQ ID NO: 58:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO: 58:

Met Asp Asp Gly Glu Thr Cys Glu Arg Cys Leu Asn Pro Leu Glu Leu
 1               5                  10                  15

Val Asn Asp Ala Val Asp Ser Cys Ile Glu Ala His Glu Glu Cys Glu
                 20                  25                  30

Glu Phe Met Glu Gly Gly Met Glu Met Leu His Val His Asn Pro Gly

-continued

```
                35                  40                  45
Asn Phe Arg Val Ser Lys Cys Val Cys Asp Ile Ala Leu Lys Glu Cys
            50                  55                  60

Leu Thr Thr His Pro Glu Met Ser Phe Lys Ser Val Lys Ala Leu Phe
65                  70                  75                  80

Phe Asp Leu Leu Ala Pro Pro Cys Phe Asp Gln Ile Ala Asp Trp Gly
                85                  90                  95

Lys Lys Lys Leu Lys Asn Lys Gln Ala Phe Pro Leu His Asp Leu Gln
                100                 105                 110

Ser Ala Ala His Ala Leu Trp Gln Thr Leu Tyr Asp Ala Val Lys Gly
            115                 120                 125

Ile Ala Gln Asp Val Gly His Ala Ala His Ser Phe Glu Lys Met Leu
            130                 135                 140

Gln
145
```

We claim:

1. Isolated DNA comprising the nucleic acid sequence as shown in Sequence ID No. 57; sequences which hybridize to the nucleic acid sequence as shown in Sequence ID No. 57 at, or between low and high stringency conditions, wherein said low stringency conditions are 3×SSC at a temperature within the range of about ambient to about 65° C., and wherein high stringency conditions are 0.1×SSC at a temperature of about 65° C.; or sequences which are degenerate as a result of the genetic code to the nucleic acid as shown in Sequence ID No. 57 and encode the same polypeptide.

2. Isolated DNA according to claim 1 comprising sequences which hybridize to the nucleic acid sequence as shown in Sequence ID No. 57 at high stringency conditions, wherein said high stringency conditions are 0.1×SSC at a temperature of about 65° C.

3. Isolated DNA according to claim 1 which is cDNA, or synthesized DNA.

4. Isolated DNA which is genomic DNA and which encodes for the same polypeptide as the DNA of claim 1.

5. A recombinant DNA construct comprising the nucleic acid sequence as shown in Sequence ID No. 57; sequences which hybridize to the sequence shown in Sequence ID No. 57 at, or between, low and high stringency conditions, wherein said low stringency conditions are 3×SSC at a temperature within the range of about ambient to about 65° C., and wherein high stringency conditions are 0.1×SSC at a temperature of about 65° C.; or sequences which are degenerate as a result of the genetic code to the sequence shown in Sequence No. 57.

6. The recombinant DNA construct according to claim 5 comprising sequences which hybridize to the nucleic acid sequence as shown in Sequence ID No. 57 at high stringency conditions, wherein said high stringency conditions are 0.1×SSC at a temperature of about 65° C.

7. The DNA construct according to claim 5 in which the DNA is cDNA or synthesized DNA.

8. The DNA construct according to claim 5 in which the DNA is genomic DNA.

9. The recombinant DNA construct according to claim 5 which is a cloning vector.

10. The recombinant DNA construct according to claim 5 which is an expression vector.

11. A transformed mammalian cell, non-mammalian vertebrate or invertebrate cell, insect cell, plant cell, bacteria or yeast comprising the recombinant DNA construct of claim 5.

12. The transformed yeast according to claim 11 which is a fungi.

13. A genetically manipulated virus comprising the nucleic acid sequence as shown in Sequence ID No. 57; sequences which hybridize to the sequence shown in Sequence ID No. 57 at, or between, low and high stringency conditions, wherein said low stringency conditions are 3×SSC at a temperature within the range of about ambient to about 65° C., and wherein high stringency conditions are 0.1×SSC at a temperature of about 65° C.; or sequences which are degenerate as a result of the genetic code to the sequence shown in Sequence No. 57.

14. The virus according to claim 13 comprising sequences which hybridize to the nucleic acid sequence as shown in Sequence ID No. 57 at high stringency conditions, wherein said high stringency conditions are 0.1×SSC at a temperature of about 65° C.

15. The virus according to claim 13 wherein the DNA is cDNA or synthesized DNA.

16. The virus according to claim 13 wherein the DNA is genomic DNA.

17. A biological control agent comprising:

(i) an insect toxin comprising at least one polypeptide which is coded for by the nucleic acid sequence as shown in Sequence ID No. 57; sequences which hybridize to the sequence shown in Sequence ID No. 57 at, or between, low and high stringency conditions, wherein said low stringency conditions are 3×SSC at a temperature within the range of about ambient to about 65° C., and wherein high stringency conditions are 0.1×SSC at a temperature of about 65° C.; or sequences which are degenerate as a result of the genetic code to the sequence shown in Sequence No. 57;

(ii) a recombinant DNA construct comprising the nucleic acid sequence as shown in Sequence ID No. 57; sequences which hybridize to the sequence shown in Sequence ID No. 57 at, or between, low and high stringency conditions, wherein said low stringency conditions are 3×SSC at a temperature within the range of about ambient to about 65° C., and wherein high stringency conditions are 0.1×SSC at a temperature of about 65° C.; or sequences which are degenerate as a result of the genetic code to the sequence shown in Sequence ID No. 57; or (iii) a transformed mammalian cell, non-mammalian vertebrate or invertebrate cell, insect cell, plant cell, bacteria, virus or yeast comprising a recombinant DNA construct comprising at least one DNA selected from the group consisting of:
the nucleic acid sequence as shown in Sequence ID No. 57,
sequences which hybridize to the sequence shown in Sequence ID No. 57 at, or between, low and high stringency conditions, wherein said low stringency conditions are 3×SSC at a temperature within the range of about ambient to about 65° C., and wherein high stringency conditions are 0.1×SSC at a temperature of about 65° C., and
sequences which are degenerate as a result of the genetic code to the sequence shown in Sequence ID No. 57.

18. A method of combating an insect pest which comprises treating the pest or its habitat with a pest-controlling effective amount of the biological control agent of claim 17.

* * * * *